(12) United States Patent
Solem et al.

(10) Patent No.: US 11,077,240 B2
(45) Date of Patent: Aug. 3, 2021

(54) DETECTION OF A DISRUPTION OF A FLUID CONNECTION BETWEEN TWO FLUID CONTAINING SYSTEMS

(71) Applicant: GAMBRO LUNDIA AB, Lund (SE)

(72) Inventors: Kristian Solem, Trelleborg (SE); Bo Olde, Lund (SE); Jan Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 830 days.

(21) Appl. No.: 15/573,285

(22) PCT Filed: Jun. 3, 2016

(86) PCT No.: PCT/EP2016/062617
§ 371 (c)(1),
(2) Date: Nov. 10, 2017

(87) PCT Pub. No.: WO2016/206946
PCT Pub. Date: Dec. 29, 2016

(65) Prior Publication Data
US 2018/0126062 A1  May 10, 2018

(30) Foreign Application Priority Data
Jun. 25, 2015  (SE) .................................. 1550881-5

(51) Int. Cl.
*A61M 1/36* (2006.01)
*A61B 5/0215* (2006.01)

(52) U.S. Cl.
CPC ....... *A61M 1/3656* (2014.02); *A61B 5/02152* (2013.01); *A61M 2205/17* (2013.01); *A61M 2205/18* (2013.01); *A61M 2205/3331* (2013.01)

(58) Field of Classification Search
CPC .............. A61M 1/3656; A61M 1/3658; A61M 1/3659; A61M 1/3661; A61M 1/3663;
(Continued)

(56) References Cited

U.S. PATENT DOCUMENTS 7,575,562 B2    8/2009  Takayuki et al.
2001/0048892 A1  12/2001 Bainbridge et al.
(Continued)

FOREIGN PATENT DOCUMENTS

EP       0328162     8/1989
JP     2010136745     6/2010
(Continued)

OTHER PUBLICATIONS

International Search Report issued in nternational Patent Application No. PCT/EP2016/062617 dated Aug. 22, 2016.
(Continued)

*Primary Examiner* — Philip R Wiest
(74) *Attorney, Agent, or Firm* — K&L Gates LLP

(57) ABSTRACT

A monitoring system (9) performs a method for detecting a disruption of a fluid connection between a first fluid containing system and a second fluid containing system. The monitoring system generates a monitoring signal (M1) which is representative of a fluid pressure in respect of the first fluid containing system and which is responsive to the disruption of the fluid connection, and a tracking signal (T1) which corresponds to and is more smoothed over time than the monitoring signal (M1). The monitoring system (9) further sets a detection range (M1L, M1H) in a given relation to the tracking signal (T1) so that the detection range (M1L, M1H) follows changes in the tracking signal (T1), and detects a condition indicative of the disruption by comparing a current pressure value of the monitoring signal (M1) to the detection range (M1L, M1H). The monitoring
(Continued)

system (9) may be connected to or part of an apparatus for blood treatment and operable to detect a disconnection of an extracorporeal blood circuit from a vascular system of a patient, e.g. downstream of a blood pump in the extracorporeal blood circuit.

28 Claims, 9 Drawing Sheets

(58) Field of Classification Search
CPC ............ A61M 1/3639; A61M 2205/17; A61M 2205/18; A61M 2205/3331; A61M 2205/3341; A61M 2205/3355; A61B 5/02152
See application file for complete search history.

(56) References Cited

U.S. PATENT DOCUMENTS

| | | | |
|---|---|---|---|
| 2003/0136181 A1* | 7/2003 | Balschat | A61M 1/16 73/40.5 R |
| 2006/0074369 A1* | 4/2006 | Oishi | A61B 5/02152 604/4.01 |
| 2009/0088683 A1 | 4/2009 | Roger et al. | |
| 2009/0292236 A1 | 11/2009 | Kleinekofort | |
| 2010/0313958 A1 | 12/2010 | Patel et al. | |
| 2011/0034814 A1 | 2/2011 | Kopperschmidt | |
| 2011/0112595 A1* | 5/2011 | Solem | G01N 33/49 607/17 |
| 2012/0277651 A1 | 11/2012 | Gruendken et al. | |
| 2013/0046226 A1 | 2/2013 | Suffritti et al. | |
| 2013/0204542 A1 | 8/2013 | Olde et al. | |
| 2014/0305513 A1 | 10/2014 | McDowell | |

FOREIGN PATENT DOCUMENTS

| | | |
|---|---|---|
| JP | 2010136841 | 6/2010 |
| WO | WO2009156174 | 12/2009 |
| WO | WO2014107656 | 7/2014 |
| WO | WO2015183975 | 12/2015 |

OTHER PUBLICATIONS

Written Opinion issued in International Patent Application No. PCT/EP2016/062617 dated Aug. 22, 2016.

* cited by examiner

DETECTION OF A DISRUPTION OF A FLUID CONNECTION BETWEEN TWO FLUID CONTAINING SYSTEMS

PRIORITY CLAIM

The present application is a National Phase of International Application No. PCT/EP2016/062617, filed on Jun. 3, 2016, which claims priority to Swedish Patent Application No. 1550881-5, filed on Jun. 25, 2015, the entire contents of each of which are being incorporated herein by reference.

TECHNICAL FIELD

The present invention relates to a technique for detecting a disruption of a fluid connection between a two fluid containing systems, based on at least one pressure signal representing fluid pressure in one of the fluid containing systems. The fluid connection may be established between an extracorporeal circuit for blood processing and the vascular system of a human subject.

BACKGROUND ART

In extracorporeal blood processing, blood is taken out of a human subject, processed (e.g. treated) and then reintroduced into the subject by means of an extracorporeal blood flow circuit ("EC circuit") which is part of a system for blood processing. Generally, the blood is circulated through the EC circuit by a blood pump. In certain types of extracorporeal blood processing, the EC circuit includes an access device for blood withdrawal (e.g. an arterial needle or catheter) and an access device for blood reintroduction (e.g. a venous needle or catheter), which are inserted into a dedicated blood vessel access (e.g. fistula, graft or catheter) on the subject. The access devices form a fluid connection between the EC circuit and the cardiovascular system of the subject. This type of EC circuit is, e.g., used in extracorporeal blood treatments such as hemodialysis, hemodiafiltration, hemofiltration, plasmapheresis, bloodbanking, blood fraction separation (e.g. cells) of donor blood, apheresis, extracorporeal blood oxygenation, assisted blood circulation, extracorporeal liver support/dialysis, ultrafiltration, heart congestion failure treatment, etc.

It is vital to minimize the risk for malfunctions in the fluid connection that may lead to a potentially life-threatening condition of the subject. A particularly serious condition may arise if the EC circuit is disrupted downstream of the blood pump while the blood pump is running, e.g. by the access device for blood reintroduction coming loose from the blood vessel access. Such a venous-side disruption, which is commonly referred to as a Venous Needle Dislodgement (VND), may cause the subject to be drained of blood within minutes. A disruption on the arterial side, e.g. by the access device for blood withdrawal coming loose from the blood vessel access, may also present a patient risk, by air being sucked into the EC circuit and transported into the cardiovascular system, causing air embolism.

Machines for extracorporeal blood treatment typically include a safety system that monitors the status of the fluid connection between the EC circuit and the subject and triggers an alarm and/or an appropriate safety action whenever a potentially dangerous situation is detected. Such safety systems may operate on a pressure signal from a pressure sensor in the EC circuit, where the fluid pressure measured by the pressure sensor is responsive to a disconnection of the EC circuit from the blood vessel access. For example, the pressure sensor may be arranged to measure the pressure level on the venous side of the EC circuit. A venous-side disconnection results in a changed venous-side pressure, which may be detected by comparing the measured pressure level with one or more alarm thresholds that define a predefined, allowable pressure range.

Conventionally, the alarm thresholds are set, automatically by the machine or manually by an operator, and subsequently acknowledged by the operator at the beginning of a treatment session and may remain fixed throughout the session. The machine may allow the operator to manually change the alarm thresholds, and the machine may automatically change the alarm thresholds when the blood flow in the EC circuit is changed.

Generally, the alarm thresholds are primarily set to avoid false negatives in the VND detection, i.e. missed alarm conditions. At the same time, it is important to avoid frequent false positives, i.e. false alarms, since every false alarm will require the attention of dialysis personnel. A difficulty in this context is that the measured pressure level may change for other reasons than a VND during a treatment session, e.g. as a result of the patient moving, variations in the blood flow rate through the EC circuit, variations in the pressure drop in the access devices, variations in the composition of the blood (e.g. hematocrit), wear in the blood pump, changes in access pressure, etc.

Thus, it is a challenge to set the alarm thresholds so as to capture all VND events while reducing the number of false alarms.

U.S. Pat. No. 7,575,562 discloses a technique aiming to reduce false alarms when comparing a venous pressure signal to alarm thresholds for VND detection. The alarm thresholds are updated based on the current signal level in the venous pressure signal at well-defined time intervals. Thereby, at least in theory, it is possible to have the alarm thresholds follow natural variations in the venous pressure signal while ensuring that a VND event is accurately detected. The time intervals may be fixed and predefined, e.g. every 2 minutes. Alternatively, the time intervals may be dynamically calculated based on the level of variation in the venous pressure signal, such that a high variability results in a shorter time interval. In this technique, it is crucial that the time intervals are selected or calculated with great care, otherwise the monitoring is likely to result in an increased number of false positives or false negatives, or both.

JP2010-136745 discloses another technique of updating the alarm thresholds used in VND detection for the purpose of reducing false alarms. The alarm thresholds, which are compared to the venous pressure signal for VND detection, are updated based on concurrent changes in an arterial pressure signal generated by a pressure sensor on the withdrawal side of the EC circuit. Specifically, JP2010-136745 proposes to update the alarm thresholds based on the tendency (moving direction) and variation (movement magnitude) of a temporal change in the arterial pressure signal. The proposed technique may be useful to suppress the number of false alarms caused by patient movement, assuming that the venous and arterial pressures signals are equally affected by patient movement, but may not compensate for other natural variations in the venous pressure signal, such as variations in the pressure drop in access device for blood return, variations in the composition of the blood (e.g. hematocrit) and wear in the blood pump. These other natural variations in the venous pressure signal need not emerge proportionally in the arterial pressure signal, which means that the proposed technique may fail to compensate for these variations and may even increase the risk for false positives and/or false negatives. The proposed technique may also require advanced calibration procedures to determine the relation between changes in the venous pressure signal and changes in the arterial pressure signal.

An alternative technique for reducing the influence of patient movement is disclosed in US2011/0034814, which proposes to generate a difference signal representing the pressure differential between the venous and arterial pressure signals and comparing the difference signal to a predefined threshold limit for VND detection. The difference signal is generated so as to be free of cyclic interferences from the blood pump and other cyclic pulse generators in the extracorporeal blood circuit. Even if this technique has a reduced sensitivity to patient movement, it is still sensitive to natural variations that only affect one of the venous and arterial pressure signals, or that have significantly different impact on these signals.

Even if the foregoing description is given in the context of extracorporeal blood processing, it is understood that a corresponding need to detect a disruption of a fluid connection between two fluid containing systems may arise in other fields of technology.

SUMMARY

It is an objective of the invention to at least partly overcome one or more of limitations of the prior art.

Another objective is to provide an alternative technique for generally detecting a disruption of a fluid connection between two fluid containing systems based on measurement of fluid pressure in one of the fluid containing systems.

Yet another objective is provide such an alternative technique which is relatively unaffected by variations in fluid pressure unrelated to the disruption.

A still further objective is provide such an alternative technique which is robust and simple to implement.

A further objective is to provide such an alternative technique which is applicable for detecting a return-side disconnection of an extracorporeal blood circuit from the vascular system of a subject.

One or more of these objectives, as well as further objectives that may appear from the description below, are at least partly achieved by monitoring systems, a method, a computer-readable medium, and an apparatus for extracorporeal blood treatment according to the independent claims, embodiments thereof being defined by the dependent claims.

A first aspect of the invention is a monitoring system for detecting a disruption of a fluid connection between a first fluid containing system and a second fluid containing system. The monitoring system comprises: a signal generating arrangement configured to generate a monitoring signal which is representative of a fluid pressure in respect of the first fluid containing system and which is responsive to the disruption of the fluid connection; and a disruption detector configured to detect a condition indicative of the disruption by comparing a current pressure value of the monitoring signal to a detection range. The signal generating arrangement is further configured to generate a tracking signal which corresponds to and is more smoothed over time than the monitoring signal, and the disruption detector is further configured to set the detection range in a given relation to the tracking signal so that the detection range follows changes in the tracking signal.

The first aspect is based on the insight that the disruption of the fluid connection results in a signal change in the monitoring signal from a reference signal level, which represents the average fluid pressure immediately before the disruption, and that this signal change occurs on a much shorter time scale than trends that may affect the reference signal level. By generating a tracking signal that corresponds to the monitoring signal but is more smoothed over time than the monitoring signal, the tracking signal will be a sufficiently accurate approximation of the reference signal level, whereas the monitoring signal will represent faster changes in fluid pressure, including changes caused by a disruption. By setting the detection range in a given relation to the tracking signal, it is ensured that the detection range approximately follows and is set with respect to the reference level. This allows the use of a relatively small detection range, since the detection range can be set in relation to the expected signal change that occurs in the monitoring signal when the fluid connection is disrupted. By using a relatively small detection range, it is possible to reduce the risk for false negatives in the disruption detection, and also to reduce the number of false positives.

Thus, the monitoring system of the first aspect is configured to be relatively unaffected by such variations in fluid pressure that are unrelated to a disruption of the fluid connection, at least such variations that emerge on a longer time scale than the disruption of the fluid connection. As will be described further below, the first aspect may be modified to further reduce false positives resulting from variations that occur in the monitoring signal on the same time scale as a disruption, e.g. by applying additional detection rules before generating an alarm or by clever selection of the monitoring signal.

The monitoring system of the first aspect is robust in the sense that the detection range is set based on a smoothed version of the monitoring signal which ensures that the detection range varies slowly and is relatively insensitive to noise and other short-term disturbances in the monitoring signal or in the one or more pressure signals that are used for generating the monitoring signal. The monitoring system is also simple to implement since it merely requires one or more pressure signals from one or more conventional pressure sensors as input. Furthermore, the monitoring system may be configured for use in a particular environment without requiring extensive calibration. The monitoring system merely needs to be set up with a detection range that is adequately matched to the expected signal change in the monitoring signal when the fluid connection is disrupted. This expected signal change may be estimated by simple preparatory testing or measurement.

The detection range may have a fixed extent and location with respect to the tracking signal during normal operation of the monitoring system. The detection range may be open-ended, and thus be defined by a single threshold value, or closed and thus defined between two threshold values. Each threshold value may be given as a respective preset offset to the tracking signal.

In a variant, the extent of the detection range may be varied during operation of the monitoring system. If the detection range is defined by one or two offsets to the tracking signal, one or both offsets may changed to vary the extent of the detection range.

The detection range may define signal values that indicate absence of a disruption and may thus be located, by the disruption detector, to include a current signal value of the tracking signal.

Further embodiments of the monitoring system are defined below and may serve the purpose of reducing the number of false positives, improving robustness, facilitating implementation, or another purpose as understood by the skilled person.

In one embodiment, the signal generating arrangement is configured to generate both the monitoring signal and the tracking signal as continuous signals. If they are digital signals, the signal generating arrangement may generate the pressure values of the monitoring and tracking signal at the same or similar rates. The disruption detector may operate to set the detection range at any rate, e.g. at the generation rate for pressure values in the tracking signal or a slower rate.

In one embodiment, the signal generating arrangement comprises a first signal filter for generating the monitoring signal and a second signal filter for generating the tracking signal. In one implementation, the first and second signal filters may define a respective lowest frequency passband extending between lower and upper limit frequencies, the upper limit frequency of the second signal filter being lower in frequency than the upper limit frequency of the first signal filter. The ratio of the upper limit frequencies of the first and second signal filters may be at least 2, at least 5, at least 10, or at least 20.

In one embodiment, the first and second signal filters comprise a respective low-pass filter, wherein the upper limit frequency is a cutoff frequency of the respective low-pass filter.

In one embodiment, at least one of the first and second signal filters comprises a moving average filter which is configured to generate a time-sequence of filtered values based on signal values in an input signal, wherein each filtered value is computed as an average of the signal values within a time window in the input signal, said moving average filter being configured to, based on a reference signal indicative of a current operating frequency of a repetitive pulse generator in the first or second fluid containing system, set the length of the time window to effectively match a given whole number of pulsations generated by the repetitive pulse generator. In one implementation, the moving average filter is included in the first signal filter and in the second signal filter, and wherein the moving average filter in the first signal filter is configured to set the length of the time window to effectively match a first number of the pulsations, and the moving average filter in the second signal filter is configured to set the length of the time window to effectively match a second number of the pulsations, and wherein the second number is larger than the first number. The ratio of the second number to the first number is at least 2, at least 5, at least 10, or at least 20.

In one embodiment, the first and second signal filters are configured to effectively remove frequency components corresponding to an operating frequency of one or more repetitive pulse generators in the first and second fluid containing systems. As used in this context, "effectively remove" is used synonymously with "sufficiently suppress" and implies that the frequency components are suppressed to such an extent that they do not interfere with the disruption detection. In one embodiment, pulsations from the respective pulse generator are effectively removed when the peak-to-peak amplitude of the pulsations in relation to the extent of the detection range is less than 50%, preferably less than 25%, and most preferably less than 10%.

In one embodiment, the signal generating arrangement comprises at least one pressure sensor and is configured to generate the monitoring signal based on at least one pressure signal produced by the at least one pressure sensor. In such an embodiment, the signal generating arrangement may be configured to generate the tracking signal based on the at least one pressure signal or the monitoring signal. Further, the signal generating arrangement may further comprise a signal conditioner configured to process the monitoring signal and/or the tracking signal, and supply the thus-processed monitoring signal and/or tracking signal to the disruption detector, said signal conditioner being configured to detect undesired peaks in the monitoring signal and/or the tracking signal and effectively remove the respective undesired peak by replacing the respective undesired peak with a signal segment that connects a starting point of the respective undesired peak with an end point of the respective undesired peak.

In one embodiment, the monitoring system is further configured to, when detecting the condition indicative of a disruption, generate a control signal for disabling one or more pulse generators in the first fluid containing system, analyze the at least one pressure signal for detection of at least one pressure pulsation originating from one or more pulse generators in the second fluid containing system, and, if said at least one pressure pulsation is deemed to be absent in the at least one pressure signal, generate an alarm signal.

In one embodiment, the disruption detector is further configured to receive a disturbance signal indicative of time points of forecasted or actual disturbances in the monitoring signal and take, based on the disturbance signal, precautionary measures to reduce the impact of the forecasted or actual disturbances on the detection of the condition indicative of the disruption. The disruption detector may be configured to, based on the time points of the forecasted or actual disturbances, determine disturbance periods and disable the detection of the condition indicative of the disruption during the respective disturbance period. The monitoring system may be further configured to, after the respective disturbance period, cause the signal generating arrangement to re-start generating the tracking signal based on the monitoring signal or the at least one pressure signal, while excluding data samples originating during the respective disturbance period. Alternatively or additionally, the disruption detector may be configured to disable the detection of the condition by one of: causing the monitoring signal to be set equal to the tracking signal during the respective disturbance period; and increasing the detection range.

In one embodiment, the disruption detector is configured to apply a disruption detection rule that requires the monitoring signal to fall outside the detection range during a predefined detection time period, and the disruption detector is configured to increase the predefined detection time period by adding an extension time period during the respective forecasted or actual disturbance.

In one embodiment, the signal generating arrangement is further configured to generate the monitoring signal to represent a functional combination of first and second pressure signals from first and second pressure sensors, the first pressure signal being responsive to the disruption of the fluid connection and the second pressure signal being non-responsive to the disruption of the fluid connection, wherein the monitoring signal is generated to represent changes in fluid pressure that are present at both the first pressure sensor and the second pressure sensor while suppressing changes in fluid pressure that are present at both of the first and second pressure sensors. In one example, the functional combination is a product of the first and second pressure signals, or first and second intermediary signals that are generated to represent the first and second pressure signals. In another example, the functional combination is difference between the first and second pressure signals or the first and second intermediary signals.

In one embodiment, the signal generating arrangement is further configured to generate an auxiliary monitoring signal, which is representative of a second fluid pressure in respect of the first fluid containing system and is non-responsive to the disruption of the fluid connection, and an auxiliary tracking signal, which corresponds to and is more smoothed over time than the auxiliary monitoring signal, and set an auxiliary detection range in a given relation to the auxiliary tracking signal so that the auxiliary detection range follows changes in the auxiliary tracking signal, wherein the disruption detection is configured to, for detecting the condition indicative of the disruption, jointly analyze the monitoring signal in relation to the detection range and the auxiliary monitoring signal in relation to the auxiliary detection range.

In one embodiment, the signal generating arrangement is further configured to generate the monitoring signal and the tracking signal so as to significantly suppress pulsations originating from one or more repetitive pulse generators in the first and second fluid containing systems.

A second aspect of the invention is a monitoring system for detecting a disruption of a fluid connection between a first fluid containing system and a second fluid containing system. The monitoring system comprises: means for generating a monitoring signal which is representative of a fluid pressure in respect of the first fluid containing system and which is responsive to the disruption of the fluid connection; and means for detecting a condition indicative of the disruption by comparing a current pressure value of the monitoring signal to a detection range. The monitoring system further comprises: means for generating a tracking signal which corresponds to and is more smoothed over time than the monitoring signal; and means for setting the detection range in a given relation to the tracking signal so that the detection range follows changes in the tracking signal.

A third aspect of the invention is a method of detecting a disruption of a fluid connection between a first fluid containing system and a second fluid containing system. The method comprises: generating a monitoring signal which is representative of a fluid pressure in respect of the first fluid containing system and is responsive to the disruption of the fluid connection; and detecting a condition indicative of the disruption by comparing a current pressure value of the monitoring signal to a detection range. The method further comprises: generating a tracking signal which corresponds to and is more smoothed over time than the monitoring signal, and setting the detection range in a given relation to the tracking signal so that the detection range follows changes in the tracking signal.

A fourth aspect of the invention is a computer-readable medium comprising processing instructions for causing a data processor to perform the method of the third aspect.

A fifth aspect of the invention is a monitoring system, comprising: a signal generating arrangement configured to generate a monitoring signal which is representative of a fluid pressure in respect of an extracorporeal blood circuit, the extracorporeal blood circuit having first and second ends for connection in fluid communication with the vascular system of a patient and comprising a blood pump for circulating blood from the first end through a blood processing device to the second end, said monitoring signal being generated to be responsive to a disconnection of the extracorporeal blood circuit from the vascular system of the patient downstream of the blood pump; and a disconnection detector configured to detect a condition indicative of the disconnection by comparing a current pressure value of the monitoring signal to a detection range. The signal generating arrangement is further configured to generate a tracking signal which corresponds to and is more smoothed over time than the monitoring signal, and the disconnection detector is further configured to set the detection range in a given relation to the tracking signal so that the detection range follows changes in the tracking signal.

In one embodiment, the signal generating arrangement is configured to generate the monitoring signal to include a time-sequence of pressure values representing one of: a return-side fluid pressure in the extracorporeal blood circuit at a location between the blood pump and the second end; a product of a return-side fluid pressure in the extracorporeal blood circuit at a location between the blood pump and the second end, and a withdrawal-side fluid pressure at a location between the first end and the blood pump; and a difference between a return-side fluid pressure in the extracorporeal blood circuit at a location between the blood pump and the second end, and a withdrawal-side fluid pressure at a location between the first end and the blood pump.

A sixth aspect of the invention is an apparatus for extracorporeal blood processing, comprising: an extracorporeal blood circuit for connection in fluid communication with the vascular system of a patient at first and second ends and comprising a blood pump for circulating blood from the first end through a blood processing device to the second end; a signal generating arrangement configured to generate a monitoring signal which is representative of a fluid pressure in respect of the extracorporeal blood circuit and which is responsive to a disconnection of the extracorporeal blood circuit from the vascular system of the patient downstream of the blood pump; and a disconnection detector configured to detect a condition indicative of the disconnection by comparing a current pressure value of the monitoring signal to a detection range. The signal generating arrangement is further configured to generate a tracking signal which corresponds to and is more smoothed over time than the monitoring signal, and the disconnection detector is further configured to set the detection range in a given relation to the tracking signal so that the detection range follows changes in the tracking signal.

Any one of the above-identified embodiments of the first aspect may be adapted and implemented as an embodiment of the second to sixth aspects.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

DETAILED DESCRIPTION OF EXAMPLE EMBODIMENTS

Figure 1:
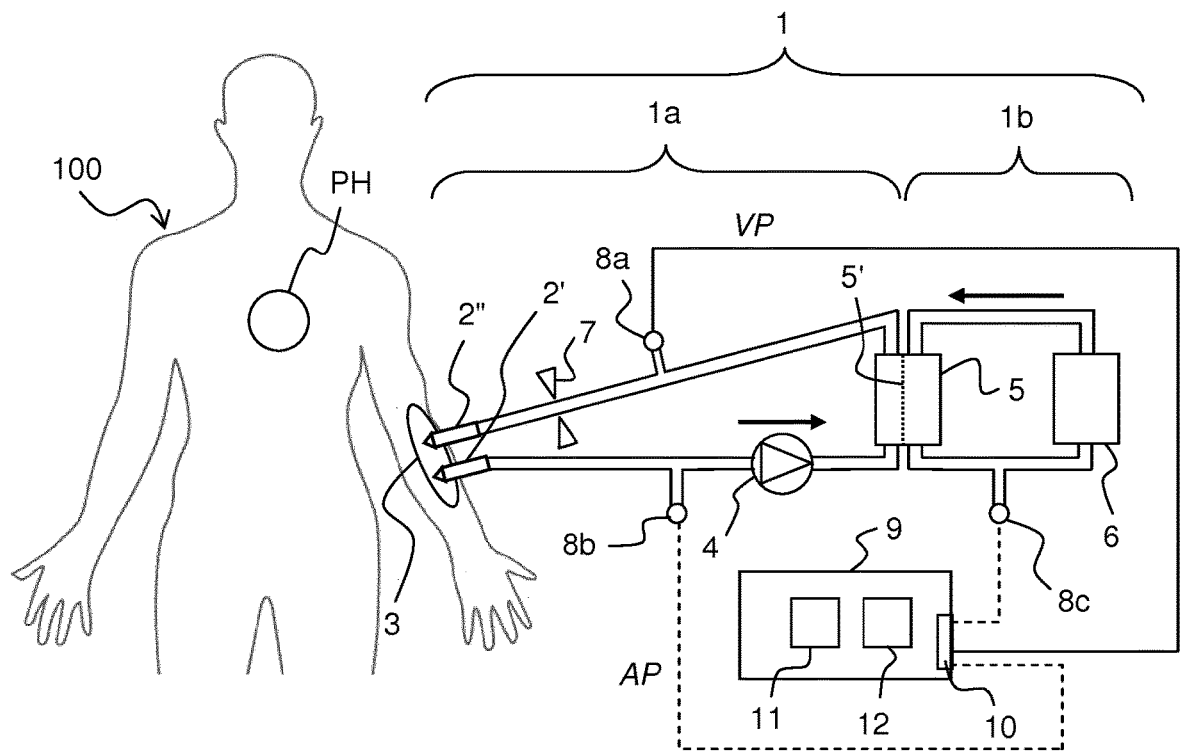
FIG. 1 is a schematic diagram of an extracorporeal blood processing apparatus attached to a human subject and comprising a disconnection detection system.

Throughout the description, the same reference numerals are used to identify corresponding elements.

Embodiments of the invention will be exemplified with reference to an apparatus for blood treatment, which is schematically depicted in FIG. 1. In the following example, the apparatus is assumed to be a dialysis system which is formed by a blood line set attached to a dialysis machine or monitor, as is well known in the art. FIG. 1 illustrates a human subject or patient 100 which is connected to an extracorporeal blood flow circuit 1a by way of access devices 2', 2" inserted into a dedicated vascular access 3 (also known as "blood vessel access") on the patient. The extracorporeal blood flow circuit 1a (denoted "EC circuit" in the following) is configured to communicate blood to and from the cardiovascular system of the patient. In the illustrated example, a blood pump 4 draws blood from the vascular access 3 via an access device 2' for blood withdrawal and pumps the blood through a blood treatment unit 5 and back to the vascular access 3 via an access device 2" for blood return. Thus, when both access devices 2', 2" are connected to the vascular access 3, the EC circuit 1a defines a blood path that starts and ends at the vascular access 3. The EC circuit 1a may be seen to comprise a "venous side" which is the part of the blood path located downstream of the blood pump 4, and an "arterial side" which is the part of the blood path located upstream of the blood pump 4. The blood pump 4 may be of any type, e.g. a rotary peristaltic pump, a linear peristaltic pump, a diaphragm pump, or a centrifugal pump.

The blood treatment unit 5 may be any type of blood filtration device, such as a coil dialyzer, a parallel plate dialyzer, a hollow fiber dialyzer, etc. For simplicity, the blood treatment unit 5 is denoted "dialyzer" in the following. The dialyzer 5 has a blood side and a treatment fluid side separated by a semipermeable membrane 5'. The blood side is connected as part of the EC circuit 1a, and the treatment fluid side is connected as part of a supply system for treatment fluid 1b (denoted "TF circuit" in the following). The TF circuit 1b is arranged to pump a treatment fluid through the treatment fluid side of the dialyzer 5, whereby solutes are transported over the membrane 5' due to a concentration gradient and/or ultrafiltrate is transported over the membrane 5' due to a pressure gradient. The skilled person understands that the TF circuit 1b may include a plurality of functional components such as a source of fresh treatment fluid, a receptacle/drain for spent treatment fluid, one or more pumps, balancing chambers, valves, heaters, conductivity sensors, etc. For simplicity, these components are collectively represented by a generic box 6 in FIG. 1.

In the example of FIG. 1, a clamp 7 is arranged on the venous-side of the EC-circuit 1a. Although not shown, a corresponding clamp may be arranged on the arterial-side. The clamp(s) 7 may be operated to block fluid passage through the blood lines, e.g. before and after a treatment session, or as part of the apparatus entering a safe state following detection of an alarm condition.

It is understood that the EC circuit 1a and the TF circuit 1b form part of the above-mentioned apparatus for blood treatment, which is schematically represented by reference numeral 1. A control unit (not shown) in the apparatus 1 controls and synchronizes the operation of, e.g., the blood pump 4, the components 6, the clamp(s) 7, as well as further components such as pumps, sensors, valves, a user interface, etc.

The EC circuit 1a includes a pressure sensor or transducer 8a (denoted "venous pressure sensor" or "venous sensor") on the venous side of the EC circuit 1a, downstream of the dialyzer 5, a pressure sensor or transducer 8b (denoted "arterial pressure sensor" or "arterial sensor") on the arterial side of the EC circuit 1a. The venous and arterial sensors 8a, 8b provide a respective time-varying signal that represents the pressure in the blood on the venous side ("venous signal") and the arterial side ("arterial signal"), respectively. In the following, the venous signal is denoted VP and the arterial signal is denoted AP. In FIG. 1, a pressure sensor or transducer 8c (denoted "TF pressure sensor" or "TF sensor") is also arranged in the TF circuit 1b to provide a time-varying signal that represents the pressure in the treatment fluid. The TF sensor 8c may have any placement in the TF circuit 1b, e.g. downstream (as in FIG. 1) or upstream of the dialyzer 5.

A monitoring device 9 is connected to the sensors 8a, 8b, 8c by way of a respective data line to acquire and process the time-varying electric pressure signals. The device 9 may be included as part of the apparatus 1 for blood treatment, and may be connected to or part of the above-mentioned control unit. Alternatively, the device 9 is separate from the apparatus 1. The dashed data lines from the arterial and TF sensors 8b, 8c to the device 9 indicate that the use of signals from these sensors is optional, as will be described further below.

Specifically, the monitoring device 9 comprises a signal interface 10 to receive at least the venous signal VP during ongoing blood treatment, and processing circuitry 11, 12 for processing the signal for the purpose of detecting a venous-side disruption of the EC circuit 1a, commonly referred to as VND. The disruption corresponds to a disconnection of the EC circuit 1a from the cardiovascular system and may be caused, e.g., by a dislodgement of the access device 2" from the vascular access 3, a rupture of a blood line on the venous-side of the EC circuit 1a, or a disconnection of a connector (not shown) which may be installed between the access device 2" and the blood line. The monitoring device 9 may also be operable to detect other malfunctions of the EC circuit 1a, e.g. that a blood line is kinked, or that the access device 2" is positioned too close to, or inserted into, a wall of the blood vessel access (known as "infiltration"). When detecting a (potential) malfunction, the device 9 may issue an alarm or warning signal and/or alert a control unit of the apparatus 1 to take appropriate action. Embodiments of the invention may e.g. be at least partly implemented by software instructions that are supplied on a computer-readable medium for execution by a processor 11 in conjunction with an electronic memory 12 in the device 9.

Generally, the EC circuit 1a and the TF circuit 1b may be seen to define a first fluid containing system, which is connected to a second fluid connection system constituted by the cardiovascular system of the patient 100. The monitoring device 9 is configured to detect a disruption of a fluid connection between the first and second fluid containing systems. In VND detection, the fluid connection is formed by the connection of the access device 2″ for blood return to the vascular access 3.

Figure 2:
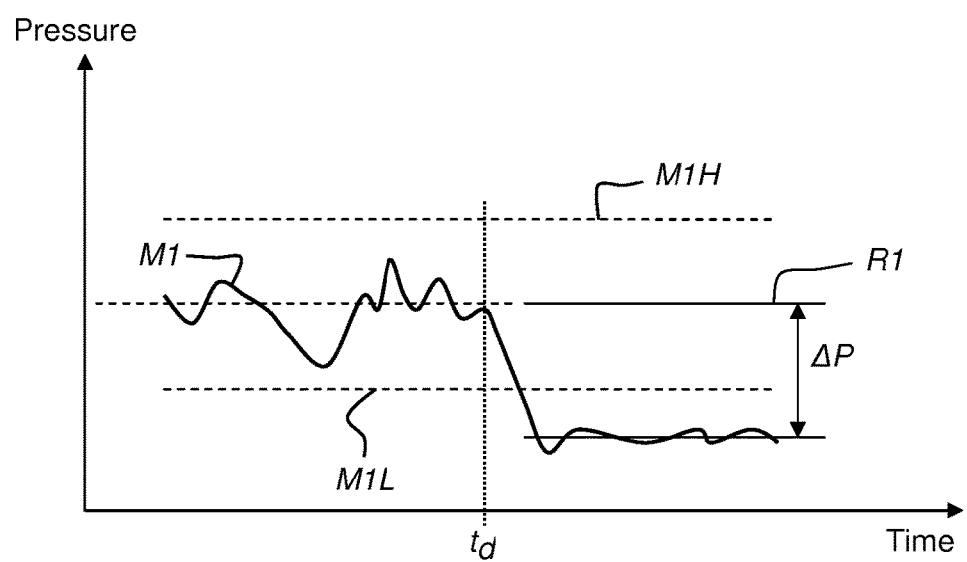
FIG. 2 illustrates a pressure signal measured in FIG. 1 during disconnection of the apparatus from the human subject.

The monitoring device 9 operates on the principle that a venous-side disruption ("VND event") results in a pressure change in the venous-side pressure measured by the venous sensor 8a. If the access device 2″ is detached from the vascular access 3 without changing the vertical position (altitude) of the access device 2″, the pressure drop is equal to the access pressure, i.e. the pressure in the vascular access 3. This principle is exemplified in FIG. 2, in which a VND event occurs at time point td. The venous-side pressure is represented by a monitoring signal M1, which is generated by filtering the venous signal VP for removal or suppression of disturbances, such as pressure variations (pulsations) originating from the blood pump 4 and other pumps, switches, valves etc in the apparatus 1. The filtering may also remove pressure variations that originate from a pulse generator PH in the patient 100 (FIG. 1), e.g. the heart or the respiratory system. Even after the filtering, the monitoring signal M1 may still exhibit relatively large variations, as seen in FIG. 2. Before the VND event, the monitoring signal M1 fluctuates around a reference pressure level, indicated by R1. The VND event causes the pressure to drop so as to fluctuate around a second reference pressure level R1-ΔP. A lower limit M1L is set intermediate the first and second reference pressure levels for detection of the VND event, and an upper limit M1H may also be set for detection of malfunctions that cause an increase in venous-side pressure, such as infiltration. Further, the upper limit M1H may be set to detect a situation in which the monitoring signal M1 increases when the access device 2″ is detached from the vascular access 3. Such a situation may occur, e.g., if the detached access device 2″ gets stuck in the bedclothes or the clothes of the patient or if the detached access device 2″ ends up at a higher altitude than the vascular access 3 (thereby increasing the hydrostatic pressure on the venous side). The limits M1L, M1H define a pressure range, denoted "detection range" in the following. The detection range thus defines an acceptable pressure range ("acceptance range") for the pressure level represented by the monitoring signal M1. A malfunction of the apparatus 1, including a VND event, may be detected when the monitoring signal M1 falls outside the detection range. It should be noted that the detection range may alternatively be defined by a single limit, to include all pressure values above or below this limit.

As understood from the foregoing, the monitoring signal M1 may exhibit variations that should not trigger an alarm. Such variations may be intermittent and cause the monitoring signal M1 to fluctuate around the first pressure reference level R1, as shown in FIG. 2, e.g. due to patient movement, movement of a blood line, a machine-related disturbance that is not sufficiently removed by the filtering, etc. The detection range is set to accommodate these short-term fluctuations as much as possible, so as to keep false alarms to a minimum.

However, it is also possible that the first pressure reference level R1 changes during a treatment session. If the first pressure reference level R1 changes in relation to the detection range, the risk for false alarms increases, especially for patients that have a relatively low access pressure (i.e. ΔP is relatively small). The first reference pressure level R1 may e.g. change as a result of a change in the posture of the patient (e.g. from sitting to lying position, or vice versa), a change in the blood flow rate through the EC circuit 1a, a change in the water removal rate through the dialyzer 5, addition of substitution fluid to the EC circuit 1a, wear in the blood pump 4, a gradual change in the blood concentration (hematocrit) during treatment, etc.

Embodiments of the invention aim to reduce the impact of changes to the first pressure reference level R1, by continuously or intermittently estimating the first pressure reference level R1 during a treatment session and adjusting the detection range accordingly. Specifically, embodiments of the invention are based on the insight that the first pressure reference level R1 may be estimated with sufficient accuracy by generating a tracking signal (cf. T1, below) which, like the monitoring signal M1, represents the venous-side pressure but is more smoothed over time than the monitoring signal M1.

Figure 3:
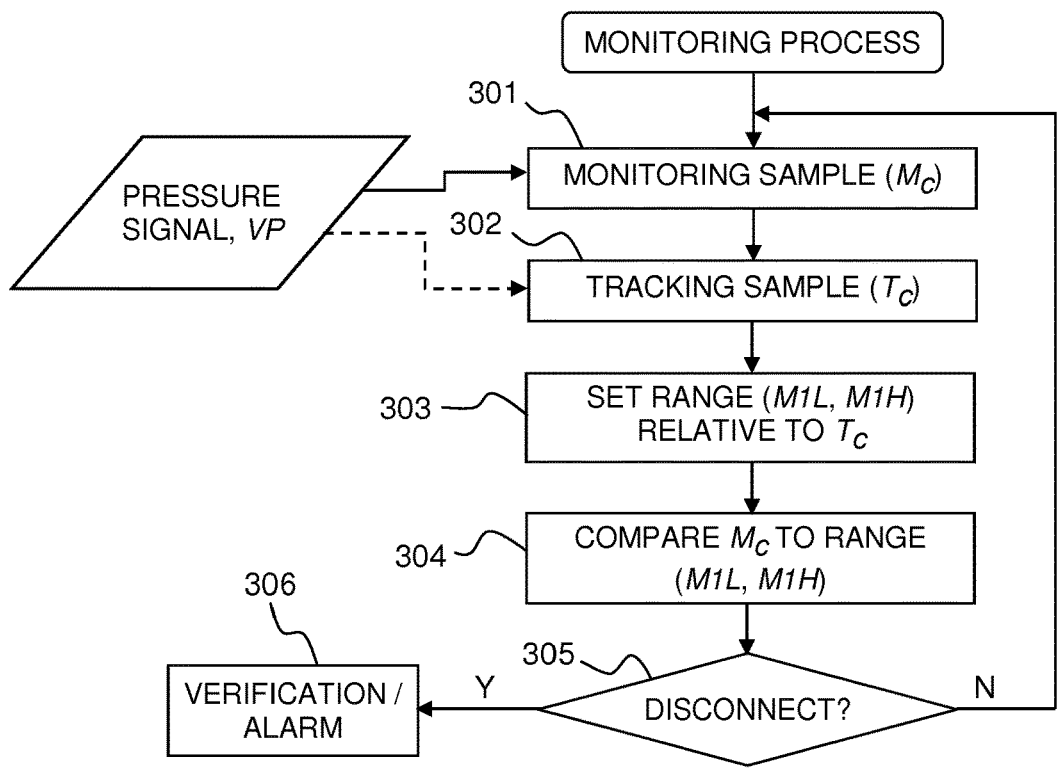
FIG. 3 is a flow chart of a monitoring process performed by the disconnection detection system according to an embodiment.
Figure 4:
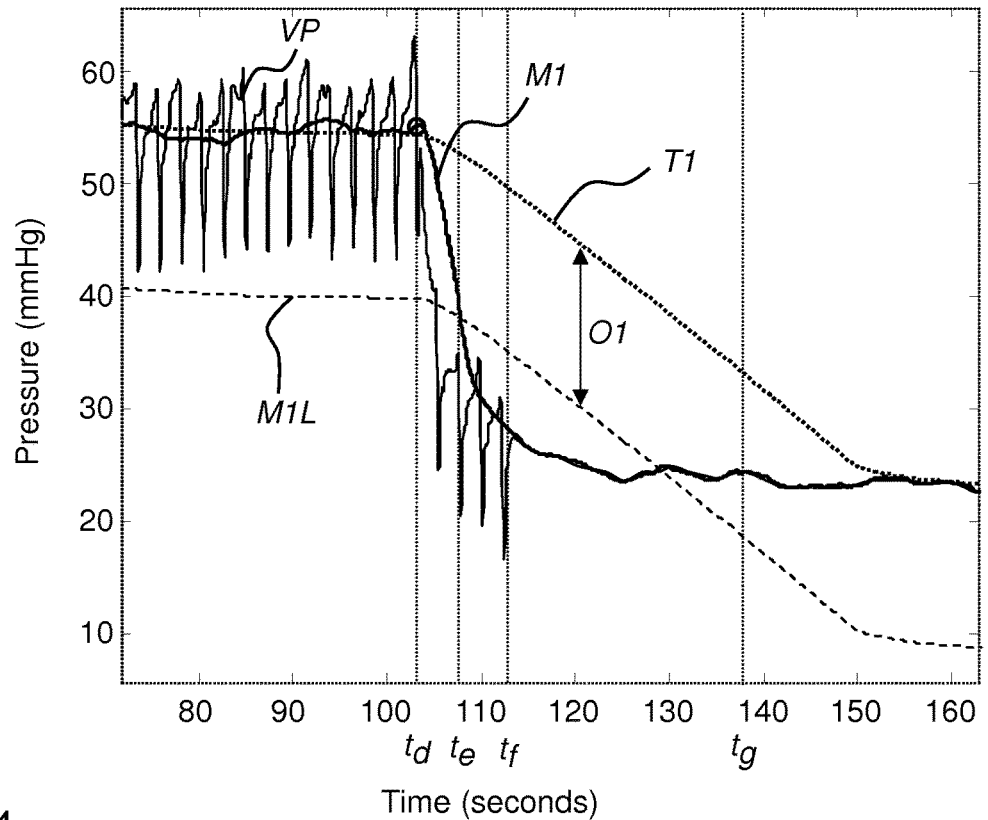
FIG. 4 is a graph of signals obtained in the apparatus of FIG. 1 during execution of the monitoring process of FIG. 3.

FIG. 3 illustrates an embodiment of a monitoring process which is executed by the device 9 in the context of FIG. 1. In the illustrated example, the monitoring process operates in real time to acquire and process data samples in the venous signal VP for VND detection by repeatedly executing steps 301-305. In step 301, a current data sample Mc of the monitoring signal M1 is generated by a first filter that operates on the venous signal VP. In step 302, a current data sample Tc of the tracking signal T1 is generated by a second filter that operates on the monitoring signal M1. Alternatively, as indicated by a dashed arrow, the second filter may operate directly on the venous signal VP to generate the current data sample Tc. Both of the current data samples Mc, Tc represent the venous-side pressure at the pressure sensor 8a, albeit on different time scales. As an example, FIG. 4 is a plot of a monitoring signal M1 and a tracking signal T1 generated by successive iterations of steps 301 and 302 for a venous signal VP. As seen, while the venous signal VP is dominated by strong pulsations ("pump pulses") which originate from the pumping strokes of the blood pump 4, the monitoring and tracking signals M1, T1 are generated to be essentially free of these pulsations. As also seen in FIG. 4, the monitoring signal M1 is generated to approximate the "DC level" of the venous signal VP, i.e. the momentary average pressure, whereas the tracking signal T1 is generated to represent a long-term pressure level (corresponding to R1 in FIG. 2). Thus, the monitoring signal M1 is generated to represent faster changes in the venous signal VP than the tracking signal T1. In other words, the monitoring and tracking signals M1, T1 are generated to represent changes in the venous signal VP on different time scales, where the time scale for the tracking signal T1 is longer than the time scale for the monitoring signal M1.

Returning to FIG. 3, step 303 operates to set the detection range relative to the current data sample Tc. Thereby, the detection range is automatically adjusted to follow changes in the tracking signal T1. For example, the detection range may be given as a respective offset value to the current data sample Tc, e.g. one offset value representing the lower limit M1L and one offset value representing the upper limit M1H. FIG. 4 shows a lower limit M1L which is set by subtracting an offset value O1 from the tracking signal T1. Alternatively, the limits M1L, M1H may be given as a respective weight value to be multiplied with the current data sample Tc. In yet another alternative, the detection range has a predefined extent which is mapped onto the current data sample Tc, e.g. by centering the detection range around the current data sample Tc. The extent of the detection range, e.g. given by the offset values, may be fixed during the monitoring process. However, it is also conceivable that the extent of the detection range is selectively modified during the monitoring process, e.g. to reduce the impact of disturbances in the signals M1, T1 on the VND detection.

Returning to FIG. 3, step 304 operates to compare the current data sample Mc with the detection range, and then proceeds to step 305 which determines if a potential VND event has occurred based on the outcome of step 304. Step 305 may apply a detection rule that requires that the monitoring signal M1 falls outside the detection range during a given detection time period, i.e. for a given number of successive repetitions of steps 301-304, before a potential VND event is declared. This may serve to reduce false alarms caused by short or spurious deviating pressure values in the monitoring signal M1. Typically, the detection time period may be 2-15 seconds, e.g. 10 seconds. If step 305 indicates that no VND event has occurred, the process returns to step 301. If step 305 declares a potential VND event, the process moves to step 306 which may operate to generate an alarm and may also trigger the apparatus 1 to enter a safe state, e.g. by shutting off the blood pump 4 and closing the clamp 7. In a variant, step 306 may perform a verification of the potential VND event before generating the alarm. The verification involves causing the apparatus 1 to shut off the blood pump 4 while keeping the clamp 7 open, and then analyzing the venous signal VP for presence of pulsations originating from a physiological pulse generator PH in the patient 100, e.g. the heart or the respiratory system. If the pulsations are absent, step 306 may conclude that a VND event indeed has occurred and generate the alarm. On the other hand, if the pulsations are found to be present, step 306 may proceed to step 301.

The operation of steps 304-306 is exemplified in FIG. 4. A VND event occurs at time point td, and step 304 detects that the monitoring signal M1 drops below the lower limit M1L at time point te. Since the monitoring signal M1 remains below the lower limit M1L during the given detection time period, which extends from time point te to time point tf, step 305 declares a potential VND event at time point tf, whereupon step 306 causes the blood pump to be stopped. Consequently, the pump pulsations cease in the signal VP. At time point tg, step 306 concludes that the heart pulsations are absent in the signal VP and issues an alarm.

In the foregoing example, the monitoring process operates in successive repetitions (iterations) of steps 301-305 until step 305 declares a potential VND event.

It is conceivable that step 304 compares the monitoring signal M1 with one or more additional alarm limits that are fixed throughout the monitoring process, or at least are not set by step 303 relative to the tracking signal T1. Such "global" alarm limits may be predefined or set by the operator or by the apparatus 1 at the start of a treatment session. Step 305 may be configured to declare a malfunction if the monitoring signal M1 falls outside such a global alarm limit, causing step 306 to issue an alarm. A global alarm limit may be set to detect malfunctions that result in a slow trend of pressure increase or decrease in the monitoring signal M1. Such malfunctions may include a gradual clogging of the access device 2" that results in a slow increase in the venous-side pressure in the EC circuit 1a, or a small, but growing, blood leakage in the EC circuit 1a (e.g. at the connection of the access device 2" to the vascular access 3) that results in a gradual decrease in the blood pressure of the patient, and hence the access pressure ΔP and thereby the venous-side pressure in the EC circuit 1a.

Figure 5:
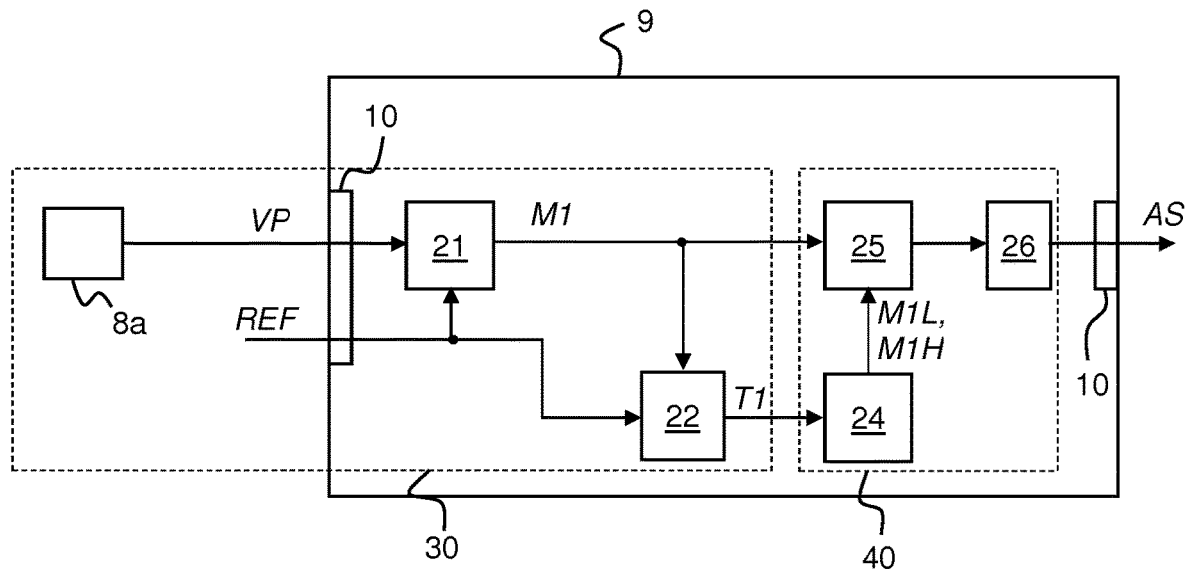
FIG. 5 is a block diagram of a disconnection detection system according to an embodiment.

FIG. 5 is a block diagram of a structure for implementing the method of FIG. 4 in the monitoring device 9. In the illustrated embodiment, the device 9 includes a signal interface 10, filter blocks 21, 22, a range setting block 24, a comparison block 25 and an alarm signal generator 26. Although not shown, a control block may be provided to synchronize the operation of the blocks 21-26, and the blocks 21-26 may exchange data via an electronic memory (cf. 12 in FIG. 1).

In the illustrated embodiment, the signal interface 10 may be of any suitable type for input and output of signals and may be implemented as a single physical unit or plural units (as shown in FIG. 5). If the device 9 is integrated in the apparatus 1, the signal interface 10 may be part of the apparatus 1 or its control unit. The signal interface 10 is configured for connection to the venous sensor 8a to receive the venous signal VP. Although not shown in FIG. 5, the device may include a block configured to pre-process the venous signal VP, and possibly one or more other incoming signals such as a reference signal REF, e.g. for AD conversion, signal amplification, removal of high frequency noise and supply voltage disturbances, etc.

A first filter block 21, which implements step 301 in FIG. 3, is arranged to receive the signal VP and generate the monitoring signal M1 as a filtered version of signal VP. A second filter block 22, which implements step 302 in FIG. 3, is arranged to receive the monitoring signal M1, and generate the signal T1 as a filtered version of signal M1. In an alternative (not shown), block 22 is instead arranged to receive the venous signal VP from the signal interface 10 and generate the signal T1 as a filtered version of the signal VP directly. Each of the filter blocks 21, 22 may have filter characteristics that are either fixed (pre-defined) or adjustable, e.g. with respect to the pumping rate of the blood pump 4 which is the source of the strong pulsations (pump pulses) that are to be effectively removed by the first and second filter blocks 21, 22. As shown in FIG. 5, blocks 21, 22 adjust their filter characteristics based on a reference signal REF which is indicative of the pumping rate of the blood pump 4. Although not shown in FIG. 5, the device 9 may include a block configured to process the reference signal REF into a current frequency value representing the rate of pump pulses in the venous signal VP. The reference signal REF may e.g. be a control signal for the speed of the blood pump 4 or the blood flow rate 4 to be generated by the blood pump 4, a pulse signal from a tachometer or the like associated with a rotor of the blood pump 4, or a pressure signal from one of the pressure sensors 8a, 8b, 8c in the apparatus 1. Thus, it is even possible to use the venous signal VP as the reference signal REF. Provided that the pump pulses dominate the pressure signal, the rate of pump pulses may be estimated based on the time difference between reference points in a pressure signal, such as maxima, minima or time points with maximum/minimum slope values.

The filter blocks 21, 22 may comprise analog filters (implemented by hardware components) or digital filters (implemented by software executed by a processor), or a combination thereof. In one embodiment, each of the filter blocks 21, 22 define at least one passband. As known in the art, a passband for a filter is a coherent range of frequencies that pass the filter. The passband extends between a lower cutoff frequency and an upper cutoff frequency, which are conventionally defined as the frequency for which the output of the filter is −3 dB of the nominal passband value. The filter blocks 21, 22 may define a plurality of passbands, but the following discussion relates to the lowest passband in terms of frequency. As noted above, the filter blocks 21, 22 may have fixed filter characteristics or filter characteristics that are adjustable with respect to the rate of pump pulses.

Figure 6A:
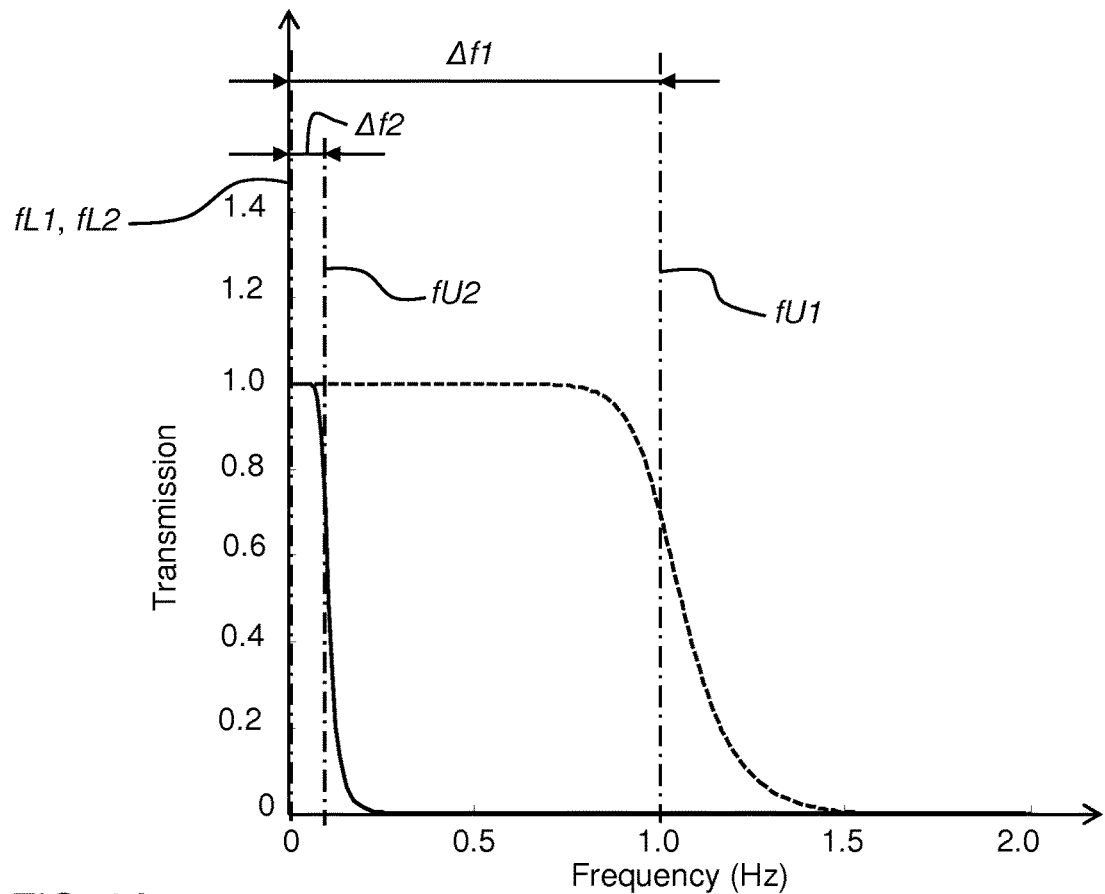
FIGS. 6A-6B are exemplifying filter characteristics of signal filters that may be implemented in the disconnection detection system of FIG. 5.

FIG. 6A shows an example of filter characteristics for the first filter block 21 (dashed lines) and second filter block 22

(solid line). As indicated, the passband 41 for the first filter block 21 extends between a lower cutoff frequency fL1 and an upper cutoff frequency fU1, and the passband Δf2 for the second filter block 22 extends between a lower cutoff frequency fL2 and an upper cutoff frequency fU2. The upper cutoff frequency fU1 is set (fixed or adjusted based on REF) to significantly suppress or remove the pump pulses, and possibly to suppress other disturbances as well, such as heart pulses. To achieve the desired properties of the tracking signal T1 vis-à-vis the monitoring signal M1, the design criterion is that fU2 should be smaller than fU1, e.g. fU2≤0.5·fU1, fU2≤0.2·fU1, fU2≤0.1·fU1 or fU2≤0.05·fU1. This design criterion is valid for all implementations of the filter blocks 21, 22. In FIG. 6A, fU1=0.1·fU2. If the upper cutoff frequency fU1 is adjusted based on REF, it may be desirable for the upper cutoff frequency fU2 to also be adjusted so as to maintain a specific ratio or difference between fU2 and fU1. However, it is conceivable that only fU1 is adjustable. In one specific embodiment, fU1 is set in the range of 0.1-1.0 Hz. The lower cutoff frequencies fL1, fL2 are not critical, but may be at or slightly above zero. The skilled person realizes that the filter characteristics in FIG. 6A may be implemented by any type of conventional low-pass (LP) filter to define the upper cutoff frequencies fU1, fU2, optionally in combination with a conventional high-pass (HP) filter to define the lower cutoff frequencies fL1, fL2 if not zero. Examples of LP filters include Butterworth filters, Chebyshev filters, Bessel filters, elliptic filters and wave filters.

Figure 6B:
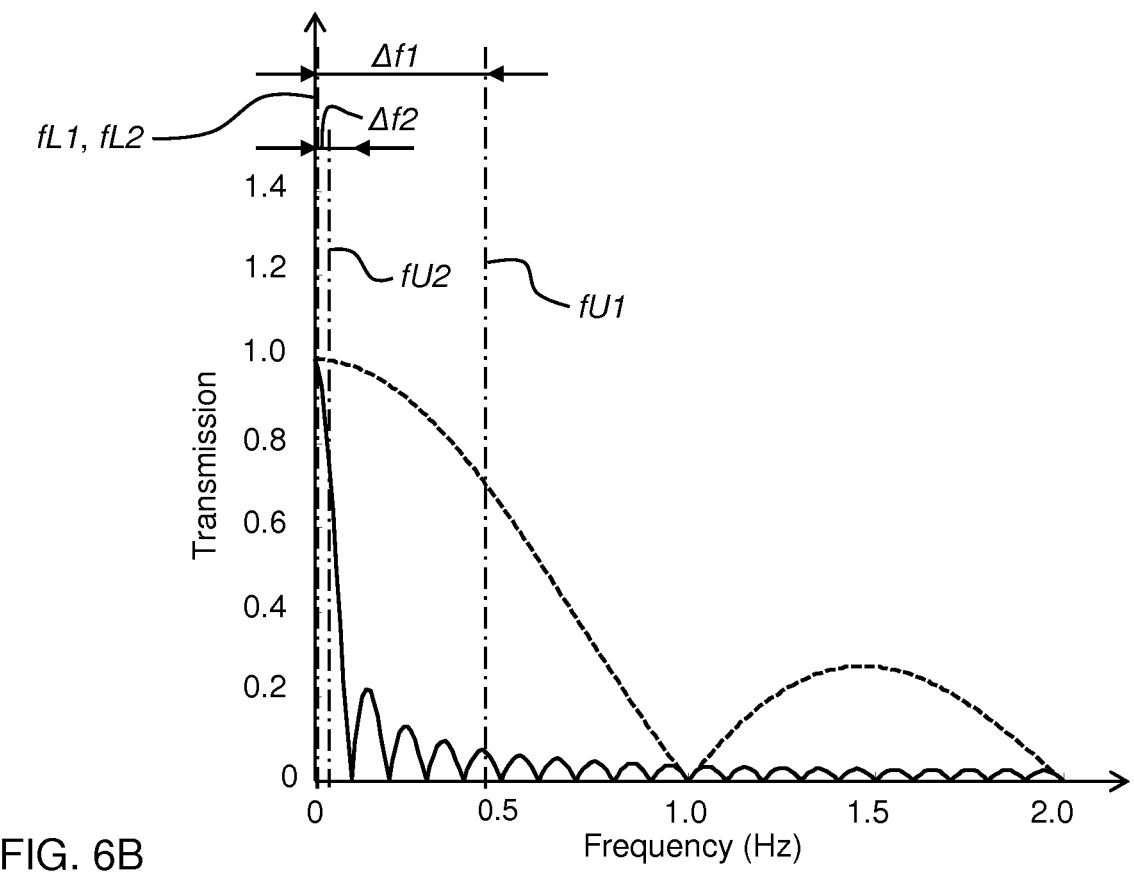
Figure 7:
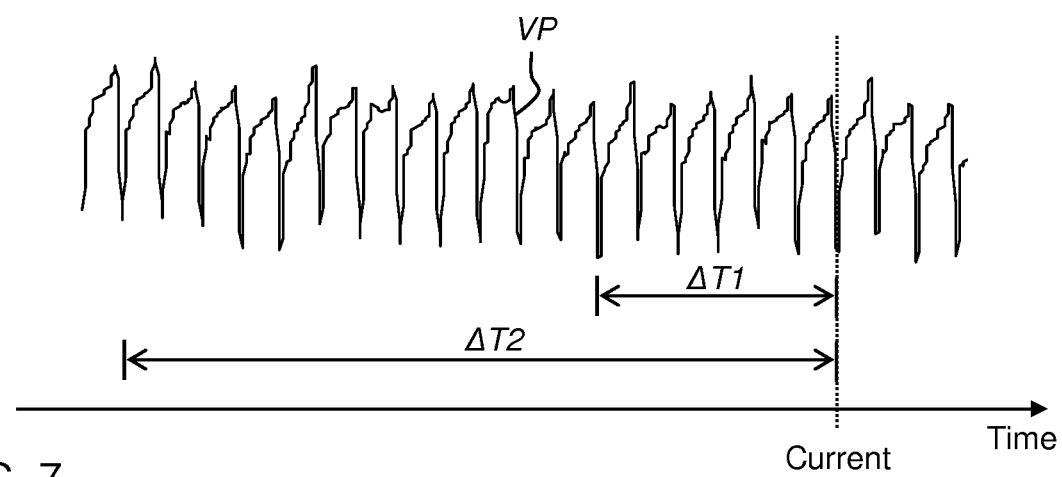
FIG. 7 illustrates use of a moving average filter for cancelling repetitive pulsations in an input signal.

FIG. 6B shows filter characteristics for the first filter block 21 (dashed lines) and second filter block 22 (solid line) when implemented by a specific type of digital LP filter, a moving average filter, which is tailored to the rate of pump pulses. Such a filter is thus adjusted based on REF. The example in FIG. 6B is shown for filters adapted to a pulse rate of 1 Hz, and illustrates the resulting passbands Δf1, Δf2. The operating principle for a moving average filter is illustrated in FIG. 7, with respect to a venous signal VP. To generate a current filtered sample, the filter computes the average of the most recent data samples within a time window in the signal VP, the length of the time window being set to correspond to a whole number of pump pulses. In practice, the number of pump pulses may deviate slightly from an integer, e.g. if the sampling rate of the signal VP is not matched to the rate of pump pulses, if there are inaccuracies in the rate of pump pulses given by REF, or if the rate of pump pulses changes between the time points when the length of the time window is adjusted. Within the context of the present disclosure, if the number of pulses within the time window deviate from an integer by less than ±10%, preferably less than ±5% and more preferably less than ±2%, the time window is considered to effectively correspond to a whole number of pump pulses. In the example of FIG. 7, the filter blocks 21, 22 operate with a respective time window ΔT1, ΔT2, which both correspond to a whole number of pump pulses in the signal VP. If the second filter block 22 operates on the monitoring signal M1, e.g. as shown in FIG. 5, time window ΔT2 will instead define data samples to be averaged in the monitoring signal M1. To achieve the desired properties of the tracking signal T1 vis-à-vis the monitoring signal M1, ΔT2 should be larger than ΔT1, e.g. ΔT2≥2·ΔT1, ΔT2≥5·ΔT1, ΔT2≥10·ΔT1 or ΔT2≥20·ΔT1.

It should be understood that the filter blocks 21, 22 may include additional filters that are designed to remove other disturbances in the venous signal VP, such as heart pulses.

Returning to FIG. 5, the device 9 further includes a range setting block 24, which implements step 303 in FIG. 3 and is arranged to receive the tracking signal T1, as generated by filter block 22. Block 24 is thereby configured to adjust the detection range to follow changes in the signal T1. A comparison block 25, which implements step 304 in FIG. 3, is arranged to receive the detection range, as set by block 24, and the monitoring signal M1, as generated by block 21. Block 25 is thereby configured to compare a current value of the signal M1 to the detection range and provide an indication whether the current value falls outside the detection range. An alarm signal generator 26, which implements steps 305-306 in FIG. 3, receives this indication and may generate an alarm signal AS to declare than a VND event has occurred. The alarm signal AS is output via the signal interface 10 and may cause the control unit of the apparatus 1 to enter the above-mentioned safe state.

As indicated by a dashed box in FIG. 5, the combination of the device 9 and the venous sensor 8a may be seen to include a signal generating arrangement 30 which generates the monitoring and tracking signals M1, T1. In the illustrated embodiment, the signal generating arrangement 30 comprises the venous sensor 8a and the filter blocks 21, 22. The device 9 may also be seen to include a disconnection or disruption detector 40, which receives the monitoring and tracking signals M1, T1 and declares a VND event. In the illustrated embodiment, the disruption generator 40 comprises the range setting block 24, the comparison block 25 and the alarm signal generator 26.

FIGS. 8A-8F illustrate alternative embodiments. For brevity of presentation, the following description will focus on differences compared to the embodiment in FIG. 5. Thus, it can be assumed that the description of FIG. 5 is equally applicable to each of FIGS. 8A-8F, unless otherwise stated.

Figure 8A:
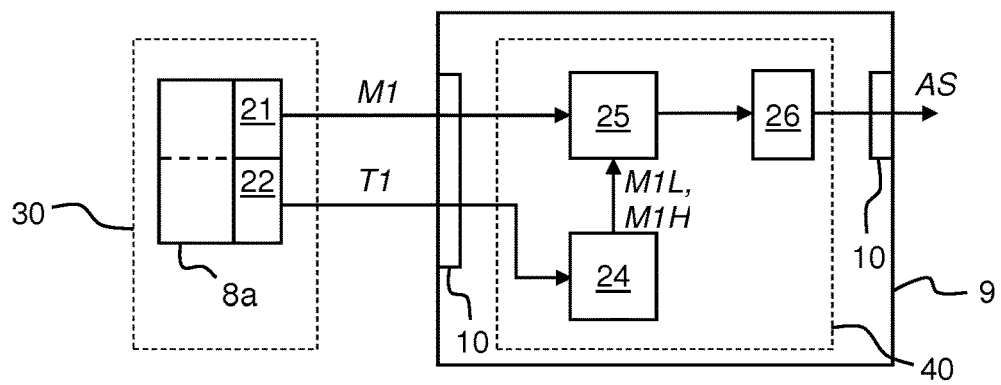
FIGS. 8A-8F are block diagrams of disconnection detection systems according to further embodiments.

In the embodiment of FIG. 8A, both the monitoring signal M1 and the tracking signal T1 are generated by the pressure sensor 8a, which thus includes the filter blocks 21, 22. In this embodiment, the filter characteristics of the filter blocks 21, 22 are fixed. The monitoring and tracking signals M1, T1 are received by the device 9 via the signal interface 10. In a variant, not shown, the pressure sensor 8a includes only the first filter block 21 and thus generates the monitoring signal M1. The second filter block 22 is arranged in the device 9 to receive and process the monitoring signal M1 for generation of the tracking signal T1.

Figure 8B:
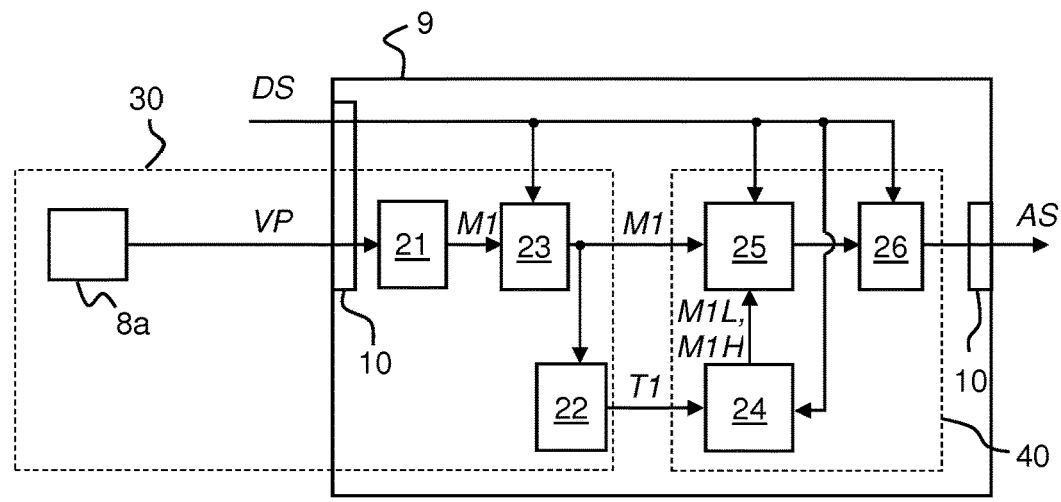

The embodiment in FIG. 8B includes a post-processing block or signal conditioner 23 which is configured to provide a cleaned version of the monitoring signal M1 that is generated by the first filter block 21. Specifically, the signal conditioner 23 operates on the monitoring signal M1 to remove or suppress intermittent disturbances that are not sufficiently removed by block 21. These disturbances may be of sufficient magnitude to result in a false alarm being generated by the disruption detector 40. The risk for false alarms may be aggravated if the tracking signal T1 is generated by filtering of the monitoring signal M1, as in FIG. 8B, since the disturbances in the monitoring signal M1 may then also migrate into the tracking signal T1 and ultimately affect the detection range that is set by block 24. Thus, the disturbances may have an impact on both the monitoring signal M1 and the detection range to which it is compared.

Figure 9:
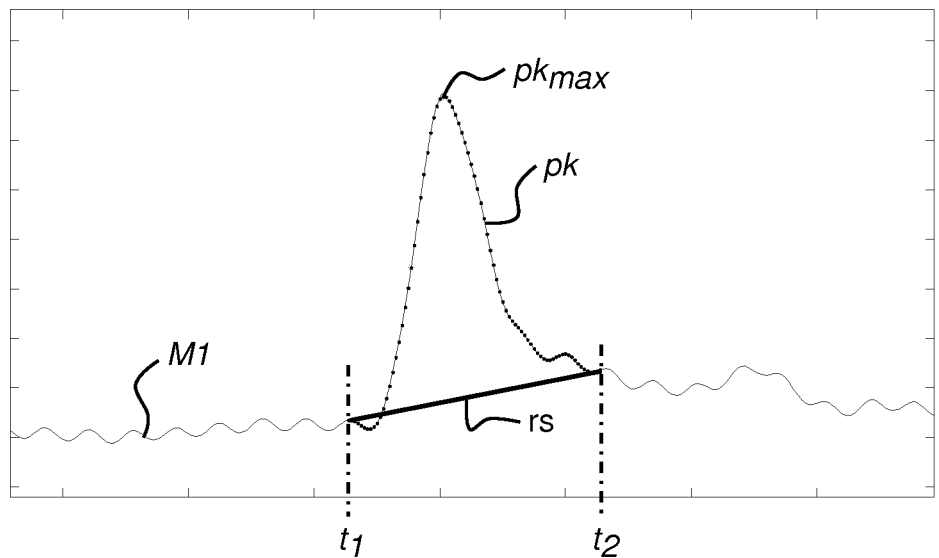
FIG. 9 illustrates a peak elimination technique applied to a monitoring signal in the embodiment of FIG. 8B.

The signal conditioner 23 may be configured to detect and suppress peaks of significant magnitude and/or specific duration in the monitoring signal M1. For example, strong intermittent peaks or fluctuations in the monitoring signal M1 may be caused by short accidental blocking of the blood flow of the EC circuit 1a, e.g. after kinking or clamping of a blood line. Such disturbances typically have a short duration, e.g. less than 2 seconds, and do not pose any significant risk for the patient, operator or machine and need therefore not result in an alarm condition. The signal conditioner 23 may be configured to detect this type of disturbance in the monitoring signal M1 using any conventional peak detection technique. When a peak is detected, the signal conditioner 23 may replace the peak by a computed segment of data samples that essentially eliminates the peak. An example is given in FIG. 9, which illustrates a peak pk in the monitoring signal M1. The signal conditioner 23 may be configured to identify the maximum $pk_{max}$ of the peak pk and estimate a starting time point t1 and an end time point t2 of the peak pk. For example, the signal conditioner 23 may obtain the time points t1, t2 by subtracting and adding a respective fixed time to the time point of $pk_{max}$. The signal conditioner 23 may then eliminate the peak pk by replacing the data samples between t1 and t2 for a computed segment of data samples, given by any suitable mathematical function. In the illustrated example, the computed segment is a linear ramp signal rs that connects the pressure values at t1 and t2. It is conceivable that the signal conditioner 23 is configured to only detect and remove peaks with specific duration, e.g. less than 2 or 5 seconds. The signal conditioner 23 need not search for maxima in the monitoring signal M1 but could instead search for sufficiently steep positive and negative flanks (e.g. derivates of sufficient absolute magnitude), optionally with a specific duration between the positive and negative flanks. In such a variant, the signal conditioner 23 may define the starting and end points t1, t2 in relation to the positive and negative flanks, respectively.

The signal conditioner 23 may also be configured to remove or suppress expected disturbances in the monitoring signal M1. Expected disturbances are tied to the operation of the apparatus 1. For example, expected disturbances in a dialysis machine may originate from changes in the flow rate of blood or treatment fluid, redirection or restriction or occlusion of fluid flow by switching of valves, degassing of the treatment fluid, UF calibration, a change of operating mode of the dialysis machine, etc. The starting and end points of a disturbance may be detected or forecasted based on one or more signals provided by the apparatus 1 or sensors attached to the apparatus 1. Such signals are collectively denoted a "disturbance signal" and designated by DS in the following. The signal conditioner 23 may receive the disturbance signal DS from the signal interface 10 and identify, in the disturbance signal DS, at least one time point of a disturbance in the monitoring signal M1. If the origin of the disturbance is known and the shape of the disturbance is reproducible, the signal conditioner 23 may be configured to retrieve (from memory 12) a template for the disturbance and subtract the template from the monitoring signal M1. Such a filtering technique is known from WO2009/156174, which is incorporated herein by this reference. Alternatively, the disturbance may be replaced for a computed segment of data samples, in the same way as described above.

In the alternative that the second filter block 22 instead is configured to generate the tracking signal T1 by filtering the venous signal VP, the device 9 may include one signal conditioner 23 for cleaning the monitoring signal M1 and one signal conditioner 23 for cleaning the tracking signal T1, where both signal conditioners 23 operate as described in the foregoing but on different signals.

A further difference between the embodiment in FIG. 8B and embodiment in FIG. 5 is that the disruption detector 40 is configured to modify its operation based on the disturbance signal DS, for the purpose of reducing the risk for false alarms. This is done by either disabling the VND detection or by reducing the likelihood that the alarm signal AS is issued. As indicated in FIG. 8B, the disturbance signal DS may be used by any one of the signal range generator 24, the comparison module 25 and the alarm signal generator 26.

In a first implementation, the comparison module 25 is configured to modify the detection range during the occurrence of the expected disturbance. This may be achieved by increasing the detection range, e.g. by increasing offset values that define the detection range. The detection range may be reset to its default value(s) after the disturbance, or be gradually reduced to the default value(s).

Figure 10:
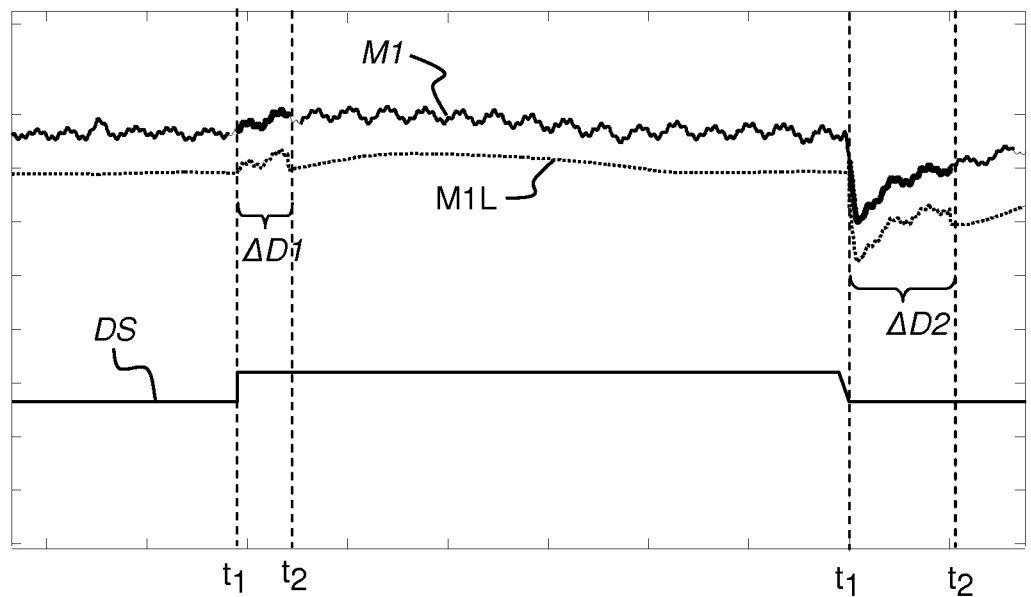
FIG. 10 illustrates use of a disturbance signal in the embodiment of FIG. 8B.

In a second implementation, the signal range generator 24 is configured to set the tracking signal T1 equal to the monitoring signal M1 during the disturbance. This will effectively disable the VND detection, since the detection range will follow the monitoring signal M1 so that the monitoring signal M1 cannot fall outside the detection range. The second implementation is exemplified in FIG. 10, which shows a disturbance signal DS that indicates the onset of two disturbances, one when the disturbance signal DS goes high and one when the disturbance signal DS goes low. FIG. 10 also shows a monitoring signal M1 which includes the disturbances (indicated by thicker lines), as well as a lower limit M1L which is set by subtraction of a fixed offset value from the tracking signal (not shown). The signal range generator 24 is configured to determine a starting time t1 for the respective disturbance, based on the disturbance signal DS. Each of the disturbance indications in the signal DS is associated with a respective expected duration ΔD1, ΔD2, allowing the signal range generator 24 to estimate an end time t2 for the respective disturbance. Alternatively, if permitted by the disturbance signal DS, the signal range generator 24 may determine the end time t2 directly from the disturbance signal DS. The signal range generator 24 then sets the tracking signal T1 equal to the monitoring signal M1 when generating the detection range in the time period between t1 and t2, causing the limit value M1L to be offset from the monitoring signal M1 during the respective disturbance, as seen in FIG. 10.

In a third implementation, the alarm signal generator 26 is configured to disable the detection of a potential VND event during the disturbance, by ignoring any data generated by the comparison module 25.

In a fourth implementation, the alarm signal generator 26 is configured to extend the detection time period, during which the monitoring signal M1 must fall outside the detection range before a potential VND event is declared. Thus, during a disturbance, the alarm signal generator 26 adds an extension time period to the predefined detection time period which is used by the alarm signal generator 26 during normal operation (in the absence of a disturbance).

In the embodiment of FIG. 8B, the generation of the tracking signal T1 in the second filter block 22 may be restarted at the end time t2 of the respective disturbance, such that the tracking signal T1 is generated to represent the venous signal VP after the disturbance. This will further serve to reduce the impact of disturbances on the accuracy of the VND monitoring.

Figure 8C:
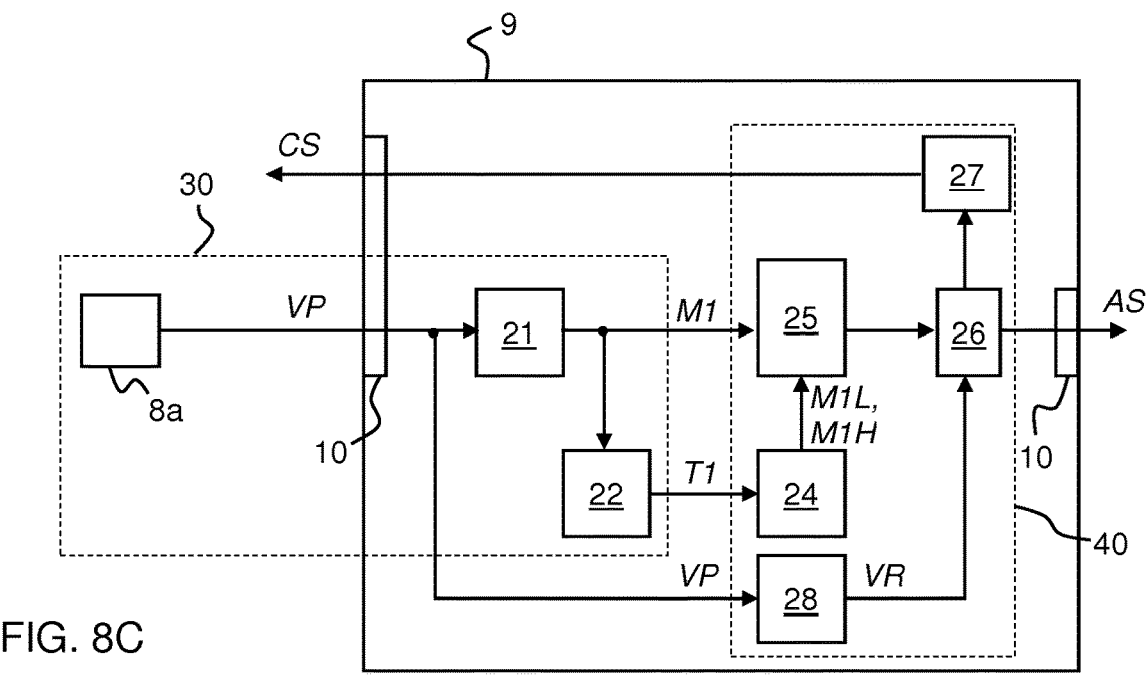

The embodiment of FIG. 8C includes a control signal generator 27 which is configured to generate a control signal CS which is output through the signal interface 10 and causes the control unit of the apparatus 1 to stop the blood pump 4. The control signal generator 27 may generate the control signal CS when the alarm signal generator 26 indicates a potential VND event, so as to start the verification as discussed in relation to step 306 in FIG. 3. Following the generation of the control signal CS, a verification block 28 is activated to monitor the venous signal VP for presence of heart pulses during a predetermined detection period. Following the detection period, the verification block 28 outputs a verification result signal VR. If the signal VR indicates a lack of heart pulses during the detection period, the alarm signal generator 26 generates the alarm signal AS, otherwise the control signal generator 27 is operated to generate the control signal CS to start the blood pump 4 and the alarm signal generator 26 resumes to analyze the output of the comparison block 25.

In a combination of the embodiments in FIGS. 8B and 8C, the device 9 may be configured to generate the control signal CS so as to cause the control unit of the apparatus 1 to reduce the speed of the blood pump 4, and thus the blood flow rate in the EC circuit 1a, during periods with disturbances detected by block 23 or during periods with disturbances indicated by the disturbance signal DS, in particular in periods with frequent disturbances. This will reduce the patient risk in case a VND event goes unnoticed by the device 9 due to the disturbances.

Figure 8D:
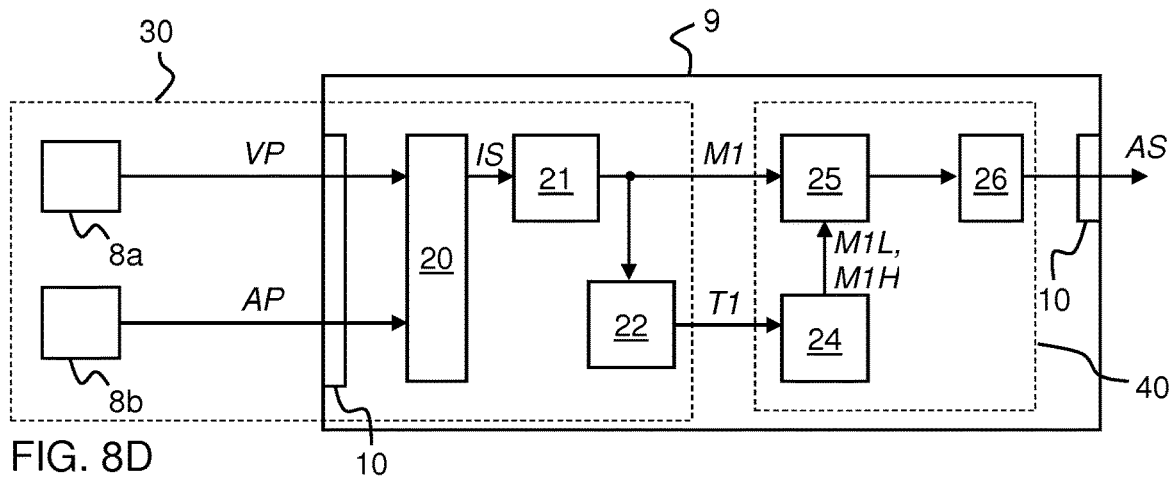

The embodiment in FIG. 8D includes both a venous sensor 8a and an arterial sensor 8b, and a combination block 20 is configured to functionally combine the venous and arterial signals VP, AP into an intermediary signal IS, which is then processed in the same way as the venous signal VP in the embodiment of FIG. 5. In one implementation, the combination block 20 generates the intermediary signal IS to represent a difference (weighted or non-weighted) between the venous and arterial signals VP, AP. Such an intermediary signal IS has been found to reduce the occurrence in the monitoring signal M1 of disturbances caused by patient movement. Patient movement will cause similar disturbances in the venous and arterial signals VP, AP, and these disturbances are thus cancelled or at least significantly reduced in the intermediary signal IS. The arterial signal AP remains essentially unaffected by VND events, which are therefore detectable in the intermediary signal IS. In a variant, the combination block 20 is instead configured to generate the intermediary signal IS to represent a product (weighted or non-weighted) of corresponding data samples in the venous and arterial signals VP, AP. It can be shown that such an intermediate signal IS is responsive to VND events while exhibiting a reduced sensitivity to disturbances that occur similarly in the venous and arterial signals VP, AP.

Figure 8E:
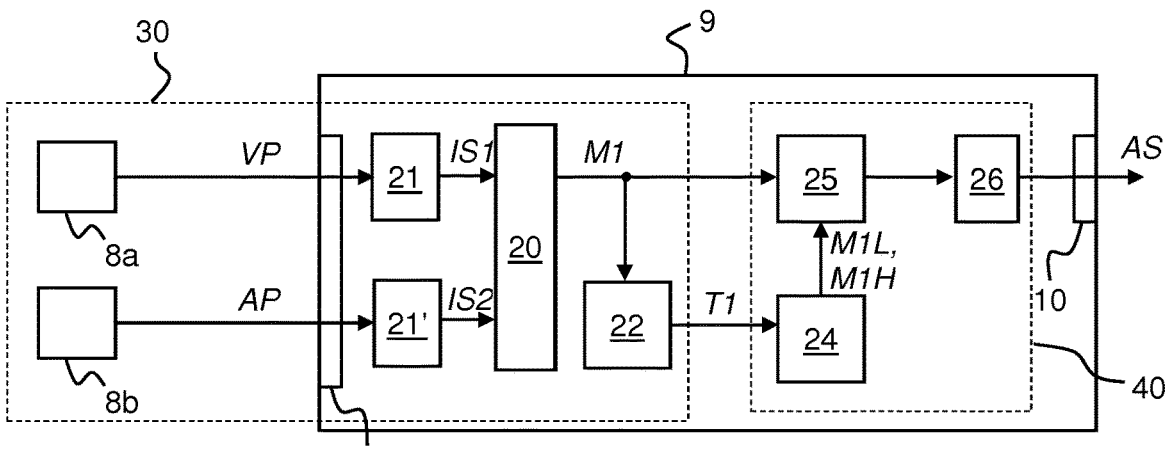

FIG. 8E shows a variant of the embodiment in FIG. 8D. The device 9 comprises two first filter blocks 21, 21' that operate on the venous signal VP and the arterial signal AP, respectively, to generate a venous intermediary signal IS1 and an arterial intermediary signal IS2. The blocks 21, 21' may, but need not, be identical. The combination block 20 is configured to functionally combine the intermediary signals IS1, IS2, as a difference or a product, which may or may not be weighted, and to output a monitoring signal M1 which is then processed in the same way as the monitoring signal M1 in the embodiment of FIG. 5. It is currently believed that the embodiment in FIG. 8E has the advantage of improving the quality of the signals that are provided to blocks 24 and 25.

Figure 11:
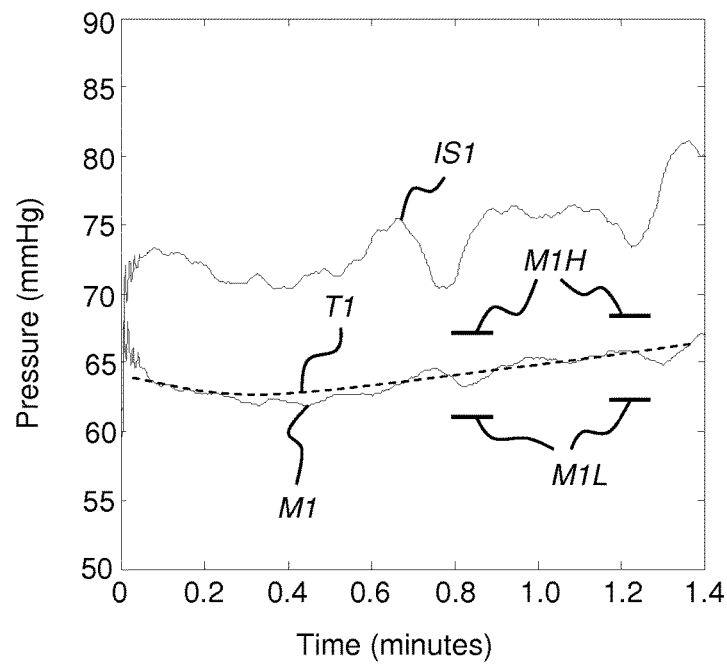
FIG. 11 illustrates signals obtained in the embodiment of FIG. 8E.

FIG. 11 illustrates the monitoring signal M1 and the tracking signal T1 that are generated in the embodiment of FIG. 8E. FIG. 11 also illustrates the venous intermediary signal IS1 generated by block 21 in FIG. 8E. The large fluctuations in the signal IS1 are the result of patient movement. As seen, these fluctuations are essentially absent in the monitoring signal M1, which thereby remains within the detection range, indicated by the limits M1L, M1H.

Figure 8F:
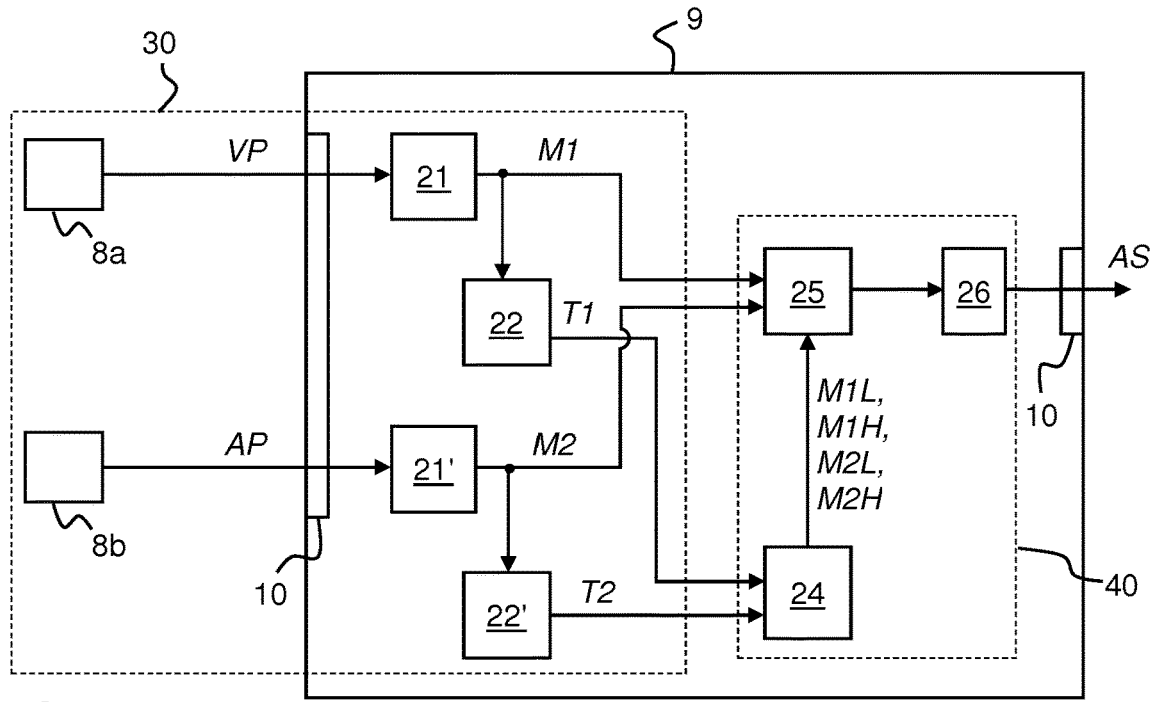

The embodiment of FIG. 8F includes both a venous sensor 8a and an arterial sensor 8b. Like the embodiment of FIG. 8E, the device 9 comprises an auxiliary first filter block 21' that operates on the arterial signal AP to generate an auxiliary or arterial monitoring signal M2 in addition to the venous monitoring signal M1 generated by the first filter block 21. An auxiliary second filter block 22' operates on the arterial monitoring signal M2 to generate an auxiliary or arterial tracking signal T2 in addition to the venous tracking signal T1 generated by the second filter block 22. The range setting block 24 is configured to set an auxiliary or arterial detection range M2L, M2H with respect to the arterial tracking signal T2, in addition to the venous detection range M1L, M1H which is set with respect to the venous tracking signal T1. The comparison block 25 is configured to compare the arterial monitoring signal M2 to the arterial detection range M2L, M2H in addition to comparing the venous monitoring signal M1 to the venous detection range M1L, M1H. The alarm signal generator 26 is configured to make a joint analysis of the venous and arterial monitoring signals M1, M2 for detection of potential VND events. The generator 26 may e.g. declare a potential VND event if the venous monitoring signal M1 falls outside the venous detection range during a detection period, provided that the arterial monitoring signal M2 does not also fall outside the arterial detection range during this detection period. If both monitoring signals M1, M2 fall outside their respective detection range, especially if both monitoring signals M1, M2 move in the same direction out of the respective detection range, it is likely that the signal changes are caused by a disturbance in both of the pressure signals VP, AP and not a VND event and no alarm signal AS should be generated. As noted in relation to FIG. 8D, such disturbances may be caused by patient movement.

Figure 12A:
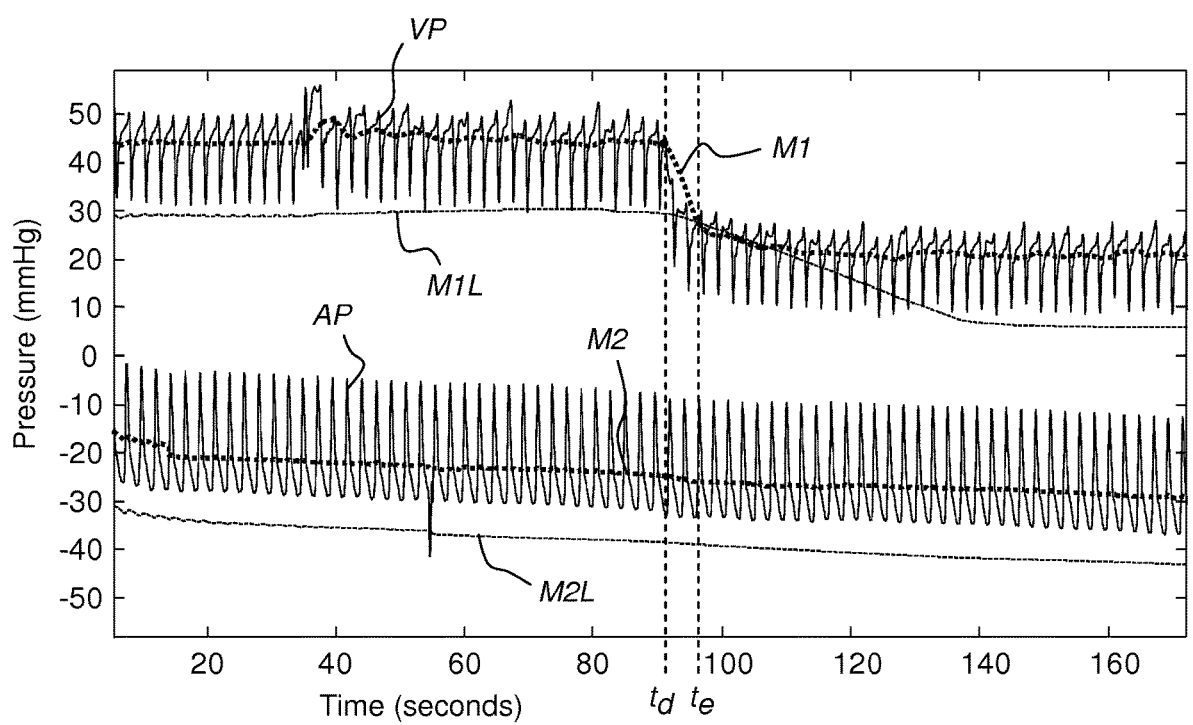
FIGS. 12A-12B illustrate signals obtained in the embodiment of FIG. 8F.
Figure 12B:
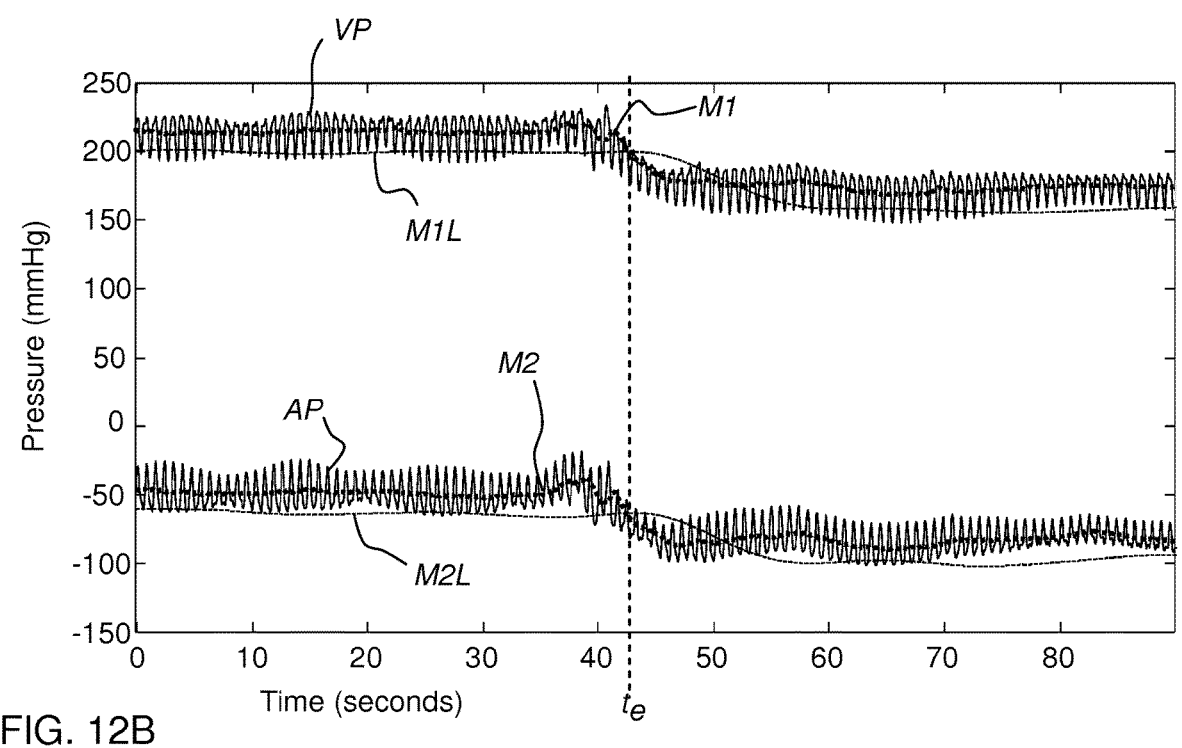

FIG. 12A shows venous and arterial monitoring signals M1, M2 generated by blocks 21, 21' in the embodiment of FIG. 8F. A VND event occurs at time point td. At time point te, block 25 detects that the venous monitoring signal M1 falls below the lower limit value M1L, which is set by block 24 in relation to a venous tracking signal (not shown) generated by block 22 to represent long-term changes in the venous signal VP. At the same time block 25 determines that the arterial monitoring signal M2 remains above the lower limit value M2L, which is set by block 24' in relation to a arterial tracking signal (not shown) generated by block 22' to represent long-term changes in the arterial signal AP. Block 26 performs a joint analysis of the output of block 25 and concludes that a potential VND has occurred. FIG. 12B shows venous and arterial monitoring signals M1, M2 generated during patient movement in the embodiment of FIG. 8F, specifically while the patient's arm (with the vascular access 3, cf. FIG. 1) is moved from a higher altitude to a lower altitude. The patient movement causes both monitoring signals M1, M2 to drop below the respective lower limit value M1L, M2L at similar time points. In FIG. 12B, this drop in both monitoring signals M1, M2 is detected by blocks 22, 22' at time point te. Since the drop occurs in both signals M1, M2, block 26 ignores the potential alarm condition.

The skilled person realizes that one or more distinguishing features of the embodiments described in relation to FIGS. 8A-8, and variants thereof, may be combined with the embodiment in FIG. 5, and variants thereof.

The monitoring device 9 may be implemented by special-purpose software (or firmware) run on one or more general-purpose or special-purpose computing devices. In this context, it is to be understood that an "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units (cf. 11 in FIG. 1), e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The device 9 may further include a system memory and a system bus that couples various system components including the system memory (cf. 12 in FIG. 1) to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The device 9 may include one or more communication interfaces (cf. 10 in FIGS. 1, 5 and 8A-8F), such as a serial interface, a parallel interface, a USB interface, a wireless interface, a network adapter, etc, as well as one or more data acquisition devices, such as an A/D converter. The special-purpose software may be provided to the device 9 on any suitable computer-readable medium, transitory or non-transitory, including a record medium or a read-only memory.

It is also conceivable that some (or all) elements/means are fully or partially implemented by dedicated hardware, such as an FPGA, an ASIC, or an assembly of discrete electronic components (resistors, capacitors, operational amplifier, transistors, filters, etc), as is well-known in the art.

It should be emphasized that the invention is not limited to digital signal processing, but could be fully implemented by a combination of analog devices.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the inventive monitoring technique is applicable also for detecting a disconnection of the access device 2' for blood removal from the vascular access 3, based on the arterial signal AP, optionally in combination with the venous signal VP, in complete analogy with the foregoing description.

Also, the inventive technique is equally applicable to single-needle dialysis.

The inventive monitoring technique is also applicable to fluid systems that contain other liquids than blood and are connected to the cardiovascular system of a human or animal subject, including systems for intravenous therapy, infusion systems, automated peritoneal dialysis (APD) systems, etc. Examples of such liquids include medical solutions, dialysis fluids, infusion liquids, water, etc.

It should be emphasized that the fluid containing systems need not involve a human or animal subject. For example, the inventive monitoring technique may be used to detect a disruption of a fluid connection between two machines or between a machine and a container.

Generally, the inventive monitoring technique is applicable for detecting a disruption of a fluid connection between any type of first and second fluid containing systems, provided that the measured fluid pressure in one of the fluid containing systems is responsive to the disruption in the sense that the disruption causes a detectable change in the measured fluid pressure.

The inventive technique need not operate on real-time data, but could be used for processing off-line data, such as a previously recorded pressure signal.

The invention claimed is:

1. A monitoring system for detecting a disruption of a fluid connection between a first fluid containing system and a second fluid containing system, the monitoring system comprising:

a signal generating arrangement configured to generate a monitoring signal which is representative of a fluid pressure in respect of the first fluid containing system and which is responsive to the disruption of the fluid connection, and a disruption detector configured to detect a condition indicative of the disruption by comparing a current pressure value of the monitoring signal to a detection range, wherein the signal generating arrangement is configured to generate a tracking signal which corresponds to and is more smoothed over time than the monitoring signal, wherein the signal generating arrangement comprises a first signal filter for generating the monitoring signal and a second signal filter for generating the tracking signal, wherein the first and second signal filters define a respective lowest frequency passband extending between lower and upper limit frequencies, wherein the upper limit frequency of the second signal filter is lower in frequency than the upper limit frequency of the first signal filter, and wherein the disruption detector is configured to set the detection range in a given relation to the tracking signal so that the detection range follows changes in the tracking signal.

2. The monitoring system of claim 1, wherein the signal generating arrangement is configured to generate the monitoring signal to represent faster fluid pressure changes than the tracking signal.

3. The monitoring system of claim 1, wherein the first and second signal filters comprises a respective low-pass filter, wherein the upper limit frequency is a cutoff frequency of the respective low-pass filter.

4. The monitoring system of claim 1, wherein the ratio of the upper limit frequencies of the first and second signal filters is at least 2.

5. The monitoring system of claim 1, wherein at least one of the first and second signal filters comprises a moving average filter which is configured to generate a time-sequence of filtered values based on signal values in an input signal, wherein each filtered value is computed as an average of the signal values within a time window in the input signal, the moving average filter being configured to, based on a reference signal indicative of a current operating frequency of a repetitive pulse generator in the first or second fluid containing system, set the length of the time window to effectively match a given whole number of pulsations generated by the repetitive pulse generator.

6. The monitoring system of claim 5, wherein the moving average filter is included in the first signal filter and in the second signal filter, and wherein the moving average filter in the first signal filter is configured to set the length of the time window to effectively match a first number of the pulsations, and the moving average filter in the second signal filter is configured to set the length of the time window to effectively match a second number of the pulsations, and wherein the second number is larger than the first number.

7. The monitoring system of claim 6, wherein the ratio of the second number to the first number is at least 2.

8. The monitoring system of claim 1, wherein the first and second signal filters are configured to effectively remove frequency components corresponding to an operating frequency of one or more repetitive pulse generators in the first and second fluid containing systems.

9. The monitoring system of claim 1, wherein the signal generating arrangement comprises at least one pressure sensor and is configured to generate the monitoring signal based on at least one pressure signal produced by the at least one pressure sensor.

10. The monitoring system of claim 9, wherein the signal generating arrangement is configured to generate the tracking signal based on the at least one pressure signal or the monitoring signal.

11. The monitoring system of claim 10, which is configured to, after the respective disturbance period, cause the signal generating arrangement to re-start generating the tracking signal based on the monitoring signal or the at least one pressure signal, while excluding data samples originating during the respective disturbance period.

12. The monitoring system of claim 9, wherein the signal generating arrangement comprises a signal conditioner configured to process and supply at least one of the monitoring signal and the tracking signal to the disruption detector, the signal conditioner being configured to detect undesired peaks in the at least one of the monitoring signal and the tracking signal and effectively remove the respective undesired peak by replacing the respective undesired peak with a signal segment that connects a starting point of the respective undesired peak with an end point of the respective undesired peak.

13. The monitoring system of claim 9, which is configured to, when detecting the condition indicative of a disruption, generate a control signal for disabling one or more pulse generators in the first fluid containing system, analyze the at least one pressure signal for detection of at least one pressure pulsation originating from one or more pulse generators in the second fluid containing system, and, if the at least one pressure pulsation is deemed to be absent in the at least one pressure signal, generate an alarm signal.

14. The monitoring system of claim 1, wherein the disruption detector is configured to receive a disturbance signal indicative of time points of forecasted or actual disturbances in the monitoring signal and take, based on the disturbance signal, precautionary measures to reduce the impact of the forecasted or actual disturbances on the detection of the condition indicative of the disruption.

15. The monitoring system of claim 14, wherein the disruption detector is configured to, based on the time points of the forecasted or actual disturbances, determine disturbance periods and disable the detection of the condition indicative of the disruption during the respective disturbance period.

16. The monitoring system of claim 15, wherein the disruption detector is configured to disable the detection of the condition by one of: causing the monitoring signal to be set equal to the tracking signal during the respective disturbance period, and increasing the detection range.

17. The monitoring system of claim 14, wherein the disruption detector is configured to apply a disruption detection rule that requires the monitoring signal to fall outside the detection range during a predefined detection time period, and wherein the disruption detector is configured to increase the predefined detection time period by adding an extension time period during the respective forecasted or actual disturbance.

18. The monitoring system of claim 1, wherein the signal generating arrangement is configured to generate the monitoring signal to represent a functional combination of first and second pressure signals from first and second pressure sensors, the first pressure signal being responsive to the disruption of the fluid connection and the second pressure signal being non-responsive to the disruption of the fluid connection, wherein the monitoring signal is generated to represent changes in fluid pressure that are present at both the first pressure sensor and the second pressure sensor while suppressing changes in fluid pressure that are present at both of the first and second pressure sensors.

19. The monitoring system of claim 18, wherein the functional combination is one of a product of the first and second pressure signals, or first and second intermediary signals that are generated to represent the first and second pressure signals, and a difference between the first and second pressure signals or the first and second intermediary signals.

20. The monitoring system of claim 1, wherein the signal generating arrangement is configured to generate an auxiliary monitoring signal, which is representative of a second fluid pressure in respect of the first fluid containing system and is non-responsive to the disruption of the fluid connection, and an auxiliary tracking signal, which corresponds to and is more smoothed over time than the auxiliary monitoring signal, and set an auxiliary detection range in a given relation to the auxiliary tracking signal so that the auxiliary detection range follows changes in the auxiliary tracking signal, wherein the disruption detection is configured to, for detecting the condition indicative of the disruption, jointly analyze the monitoring signal in relation to the detection range and the auxiliary monitoring signal in relation to the auxiliary detection range.

21. The monitoring system of claim 1, wherein the signal generating arrangement is configured to generate the monitoring signal and the tracking signal so as to significantly suppress pulsations originating from one or more repetitive pulse generators in the first and second fluid containing systems.

22. A monitoring system for detecting a disruption of a fluid connection between a first fluid containing system and a second fluid containing system, the monitoring system comprising:
  a first signal generating arrangement including a first signal filter for generating a monitoring signal which is representative of a fluid pressure in respect of the first fluid containing system and which is responsive to the disruption of the fluid connection;

a detector for detecting a condition indicative of the disruption by comparing a current pressure value of the monitoring signal to a detection range;

a second signal generating arrangement including a second signal filter for generating a tracking signal which corresponds to and is more smoothed over time than the monitoring signal; and a signal range generator for setting the detection range in a given relation to the tracking signal so that the detection range follows changes in the tracking signal, wherein at least one of the first and second signal filters comprises a moving average filter which is configured to generate a time-sequence of filtered values based on signal values in an input signal, wherein each filtered value is computed as an average of the signal values within a time window in the input signal, the moving average filter being configured to, based on a reference signal indicative of a current operating frequency of a repetitive pulse generator in the first or second fluid containing system, set the length of the time window to effectively match a given whole number of pulsations generated by the repetitive pulse generator.

23. A method of detecting a disruption of a fluid connection between a first fluid containing system and a second fluid containing system, the method comprising:

generating, via a first signal filter, a monitoring signal which is representative of a fluid pressure in respect of the first fluid containing system and is responsive to the disruption of the fluid connection;

detecting a condition indicative of the disruption by comparing a current pressure value of the monitoring signal to a detection range;

generating, via a second signal filter, a tracking signal which corresponds to and is more smoothed over time than the monitoring signal; and setting the detection range in a given relation to the tracking signal so that the detection range follows changes in the tracking signal, wherein the first and second signal filters define a respective lowest frequency passband extending between lower and upper limit frequencies, wherein the upper limit frequency of the second signal filter is lower in frequency than the upper limit frequency of the first signal filter.

24. A computer-readable medium comprising processing instructions for causing a data processor to perform the method of claim 23.

25. A monitoring system comprising:

a signal generating arrangement configured to generate, via a first signal filter, a monitoring signal which is representative of a fluid pressure in respect of an extracorporeal blood circuit, the extracorporeal blood circuit having first and second ends for connection in fluid communication with the vascular system of a patient and comprising a blood pump for circulating blood from the first end through a blood processing device to the second end, the monitoring signal being generated to be responsive to a disconnection of the extracorporeal blood circuit from the vascular system of the patient downstream of the blood pump; and a disconnection detector configured to detect a condition indicative of the disconnection by comparing a current pressure value of the monitoring signal to a detection range, wherein the signal generating arrangement is configured to generate, via a second signal filter, a tracking signal which corresponds to and is more smoothed over time than the monitoring signal, wherein the first and second signal filters define a respective lowest frequency passband extending between lower and upper limit frequencies, wherein the upper limit frequency of the second signal filter is lower in frequency than the upper limit frequency of the first signal filter, and wherein the disconnection detector is configured to set the detection range in a given relation to the tracking signal so that the detection range follows changes in the tracking signal.

26. The monitoring system of claim 25, wherein the signal generating arrangement is configured to generate the monitoring signal to include a time-sequence of pressure values representing one of:

a return-side fluid pressure in the extracorporeal blood circuit at a location between the blood pump and the second end;

a product of a return-side fluid pressure in the extracorporeal blood circuit at a location between the blood pump and the second end, and a withdrawal-side fluid pressure at a location between the first end and the blood pump; and a difference between a return-side fluid pressure in the extracorporeal blood circuit at a location between the blood pump and the second end, and a withdrawal-side fluid pressure at a location between the first end and the blood pump.

27. An apparatus for extracorporeal blood processing comprising:

an extracorporeal blood circuit for connection in fluid communication with the vascular system of a patient at first and second ends and comprising a blood pump for circulating blood from the first end through a blood processing device to the second end;

a signal generating arrangement configured to generate, via a first signal filter, a monitoring signal which is representative of a fluid pressure in respect of the extracorporeal blood circuit and which is responsive to a disconnection of the extracorporeal blood circuit from the vascular system of the patient downstream of the blood pump; and a disconnection detector configured to detect a condition indicative of the disconnection by comparing a current pressure value of the monitoring signal to a detection range, wherein the signal generating arrangement is configured to generate, via a second signal filter, a tracking signal which corresponds to and is more smoothed over time than the monitoring signal, wherein at least one of the first and second signal filters comprises a moving average filter which is configured to generate a time-sequence of filtered values based on signal values in an input signal, wherein each filtered value is computed as an average of the signal values within a time window in the input signal, the moving average filter being configured to, based on a reference signal indicative of a current operating frequency of a repetitive pulse generator in the first or second fluid containing system, set the length of the time window to effectively match a given whole number of pulsations generated by the repetitive pulse generator, and wherein the disconnection detector is configured to set the detection range in a given relation to the tracking signal so that the detection range follows changes in the tracking signal.

28. A method of detecting a disruption of a fluid connection between a first fluid containing system and a second fluid containing system, the method comprising:
- generating, via a first signal filter, a monitoring signal which is representative of a fluid pressure in respect of the first fluid containing system and is responsive to the disruption of the fluid connection;
- detecting a condition indicative of the disruption by comparing a current pressure value of the monitoring signal to a detection range;
- generating, via a second signal filter, a tracking signal which corresponds to and is more smoothed over time than the monitoring signal; and
- setting the detection range in a given relation to the tracking signal so that the detection range follows changes in the tracking signal,
- wherein at least one of the first and second signal filters comprises a moving average filter which is configured to generate a time-sequence of filtered values based on signal values in an input signal, wherein each filtered value is computed as an average of the signal values within a time window in the input signal, the moving average filter being configured to, based on a reference signal indicative of a current operating frequency of a repetitive pulse generator in the first or second fluid containing system, set the length of the time window to effectively match a given whole number of pulsations generated by the repetitive pulse generator.

\* \* \* \* \*